United States Patent [19]

Klessing et al.

[11] Patent Number: 4,542,137
[45] Date of Patent: Sep. 17, 1985

[54] ALKYLAMINODESOXY-1.4;3.6-DIANHYDROHEXITOL NITRATES SUBSTITUTED BY PURINE BASES AND PHARMACEUTICAL COMPOSITIONS

[75] Inventors: Klaus Klessing, Ettlingen; Shyam S. Chatterjee, Karlsruhe, both of Fed. Rep. of Germany

[73] Assignee: Dr. Willmar Schwabe GmbH & Co., Karlsruhe, Fed. Rep. of Germany

[21] Appl. No.: 285,425

[22] Filed: Jul. 20, 1981

[30] Foreign Application Priority Data

Jul. 25, 1980 [DE] Fed. Rep. of Germany ....... 3028272

[51] Int. Cl.$^4$ .................... A61K 31/52; C07D 473/08
[52] U.S. Cl. .................................... 514/265; 544/268; 544/277; 549/464
[58] Field of Search ................ 544/268, 277; 424/251

[56] References Cited

U.S. PATENT DOCUMENTS

| | | | |
|---|---|---|---|
| 2,852,507 | 9/1958 | Goldman et al. | 544/277 |
| 4,000,137 | 12/1976 | Duonch et al. | 544/277 |
| 4,087,603 | 5/1978 | Hamill et al. | 544/277 |
| 4,321,376 | 3/1982 | Otani et al. | 544/277 |
| 4,413,122 | 11/1983 | Klessing | 544/377 |

FOREIGN PATENT DOCUMENTS

| | | | |
|---|---|---|---|
| 1090358 | 11/1967 | United Kingdom | 544/277 |
| 1090359 | 11/1967 | United Kingdom | 544/277 |

OTHER PUBLICATIONS

Klessing et al., "Chemical Abstracts", vol. 96, 1982, Col. 96:218190r.

*Primary Examiner*—Glennon H. Hollrah
*Assistant Examiner*—James H. Turnipseed
*Attorney, Agent, or Firm*—Toren, McGeady, Stanger, Goldberg & Kiel

[57] ABSTRACT

Alkylaminodesoxy-1.4;3.6-dianhydrohexitol nitrates substituted by purine bases of the general formula I,

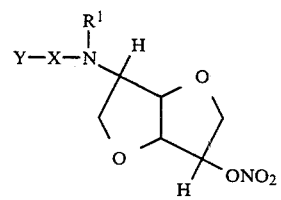

wherein $R^1$ signifies a hydrogen atom or a lower alkyl group with 1 to 4 C-atoms, X a straight-chained or branched alkyl or hydroxyalkyl group with 1 to 7 C-atoms, Y a 1,3-dialkylxanthin-7-yl or a 3,7-dialkylxanthin-1-yl group, each with straight or branched-chained alkyl groups with 1 to 5 C-atoms, or an adenin-9-yl group, as well as their physiologically acceptable acid-addition salts. Process for the preparation of said compounds and pharmaceutical compositions containing said compounds.

22 Claims, No Drawings

ALKYLAMINODESOXY-1.4;3.6-DIANHYDROHEXITOL NITRATES SUBSTITUTED BY PURINE BASES AND PHARMACEUTICAL COMPOSITIONS

The invention concerns alkylaminodesoxy-1.4;3.6-dianhydrohexitol nitrates substituted by purine bases of the general formula I,

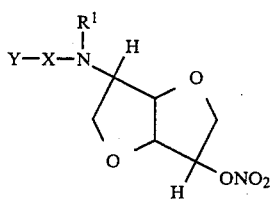 (I)

wherein $R^1$ signifies a hydrogen atom or a lower alkyl group with 1 to 4 C-atoms, X a straight-chained or branched alkyl or hydroxyalkyl group with 1 to 7 C-atoms and Y a 1,3-dialkylxanthin-7-yl or 3,7-dialkylxanthin-1-yl group, each with straight or branched chained alkyl groups with 1 to 5 C-atoms, or an adenin-9-yl group, as well as their physiologically acceptable acid-addition salts.

The basic structure of these compounds consists of one of the stereoisomeric 1.4;3.6-dianhydrohexitols convertible into one another by epimerisation, namely, either 1.4;3.6-dianhydro-L-iditol (="isoidide") (II),

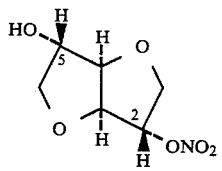 (II)

in which the OH groups in the 2- and 5-position each have the exo configuration, or 1.4;3.6-dianhydro-D-glucitol (="isosorbide") (III)

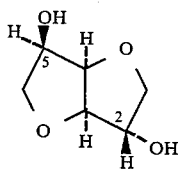 (III)

which has one 2-exo-positioned and one 5-endo-positioned OH group and thus—in the case of different substituents in the 2- and 5-position—occurs in two isomeric Finally, the basic structure of some compounds consists of 1.4;3.6-dianhydro-D-mannitol (="isomannide") (IV)

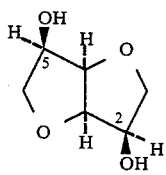 (IV)

which has two endo-standing OH groups.

In contradistinction to the glucitol derivatives, in the case of the iditol and mannitol derivatives, a differentiation between the 2- and 5-substituents is not possible because the $C^2$-atom, in the case of rotation of the molecule through 180°, becomes the $C^5$-atom so that references to the 5-position or 2-position of the substituents is, in the case of these derivatives, superfluous. However, for a better comparison of the structures of the individual compounds with the general formulae, the isoidide derivatives are here all referred to as 5-aminoisoidide derivatives since they result from isosorbide derivatives substituted in the 5-position. Correspondingly, the isomannide acyl derivatives employed as starting compounds are referred to as 2-acylisomannide derivatives since the isosorbide derivatives substituted in the 2-position are prepared from them.

A brief summary of the stereoisomerism of the 1.4;3.6-dianhydrohexitols is given by J. A. Mills in Advances in Carbohydrate Chem., 10, 1–53 (1955).

Furthermore, the invention concerns processes for the preparation of the initially mentioned alkylamino-1.4;3.6-dianhydrohexitol mononitrates substituted by purine bases, as well as pharmaceutical compositions which contain the compounds according to the invention.

The nitrates of 1.4;3.6-dianhydro-D-glucitol (also called 1.4;3.6-dianhydro-D-sorbitol) are known, e.g. from U.S. patent specification No. 3,886,186, namely, not only the 2- and 5-mononitrates but also the 2,5-dinitrate of isosorbide. These nitrates, especially the dinitrate, which is already commercially available as a medicament, are pharmacologically active substances with haemodynamic, vasodilatory and anti-anginous effectiveness which are especially used in the case of coronary insufficiency and for the treatment of angina pectoris.

The pharmokinetics of the dinitrate and of the mononitrates of isosorbide, isomannide and isoidide were described by Bogaert and Rosseel in Naunyn-Schmiedeberg's Arch. Pharmacol., 275, 339 (1972).

However, it has been shown that the nitrates cause unpleasant side effects, especially headaches. Furthermore, the mononitrates are more poorly resorbable than, for example, isosorbide dinitrate (ISDN). In addition, the dinitrates of isosorbide, isomannide and isoidide can only be prepared and handled with special precautionary measures since they are explosive.

Thus, a need existed for the making available of new pharmaceutical agents with the same activity spectrum but which do not display the mentioned disadvantages and for the provision of new 1.4;3.6-dianhydrohexitol mononitrates, which can be used as active components of such pharmaceutical agents.

The task forming the basis of the invention consists in the satisfying of the indicated need, the solution of this task in the making available of the substances according to the invention.

Consequently, the subject of the invention are 1.5-alkylamino-5-desoxy-1.4;3.6-dianhydro-L-iditol 2-nitrates substituted by purine bases of the general formula V,

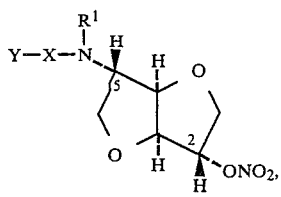

wherein $R^1$ signifies a hydrogen atom or a lower alkyl group with 1 to 4 C-atoms, X a straight-chained or branched alkyl or hydroxyalkyl group with 1 to 7 C-atoms, Y a 1,3-dialkylxanthin-7-yl or 3,7-dialkylxanthin-1-yl group, in each case with straight or branched chained alkyl groups with 1 to 5 C-atoms, or an adenin-9-yl group, as well as their physiologically acceptable acid-addition salts;

2. 5-alkylamino-5-desoxy-1.4;3.6-dianhydro-D-glucitol 2-nitrates substituted by purine bases of the general formula VI

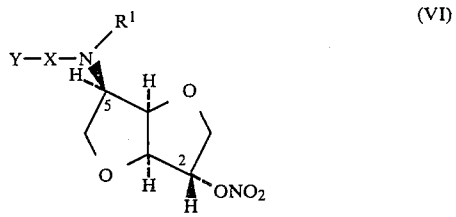

wherein $R^1$, X and Y possess the meanings mentioned under (1.), as well as their physiologically acceptable acid-addition salts;

3. 2-alkylamino-2-desoxy-1.4.;3.6-dianhydro-D-glucitol 5-nitrates substituted by purine bases of the general formula VII

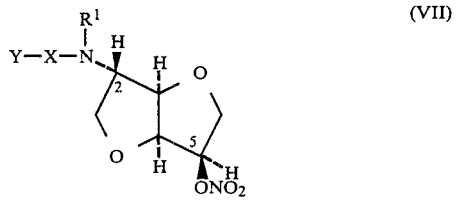

wherein $R^1$, X and Y possess the meanings given under (1.), as well as their physiologically acceptable acid-addition salts;

4. 5-alkylamino-5-desoxy-1.4;3.6-dianhydro-D-mannitol 2-nitrates substituted by purine bases of the general formula VIII

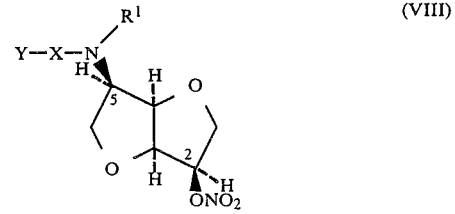

wherein $R^1$, X and Y possess the meanings given under (1.), as well as their physiologically acceptable acid-addition salts.

The compounds according to the invention possess coronary flowthrough-increasing, spasmolytic, blood-pressure-lowering, negative inotropic and heart frequency lowering as well as, in some cases, anti-arrhythmic and thrombocyte aggregation-inhibiting effectiveness. They are suitable for the treatment of coronary diseases, for the treatment and prophylaxis of angina pectoris attacks, for the post-treatment of heart infarcts and for the treatment of heart insufficiencies. The new compounds possess a good therapeutic range. The oral absorption is especially good and the period of activity is long. Furthermore, they bring about an improvement of the peripheral blood flow and of the brain blood flow.

The handling and preparation of the compounds according to the invention is much less dangerous than, for example, in the case of the known ISDN, because they are not explosive.

In the 1.4;3.6-dianhydrohexitol basic structure, the compounds according to the invention possess 4 asymmetric C-atoms and are present in optically-active form since, as starting material, there are used optically pure 1.4;3.6-dianhydrohexitols which are easily obtainable from naturally-occurring sugar alcohols.

The compounds according to the invention can be prepared starting from the epimeric, unsubstituted 1.4;3.6-dianhydrohexitols, thus starting from L-isoidide, D-isosorbide and D-isomannide, whereby in the case of D-isosorbide as starting compound, two different synthesis routes are possible.

According to the invention, the first route consists in that the corresponding 1.4;3.6-dianhydrohexitol is converted with a sulphonic acid chloride, preferably with methanesulphonic acid chloride or toluenesulphonic acid chloride, in a suitable anhydrous solvent and in the presence of an adjuvant base, preferably in pyridine or in chloroform/triethylamine, at reduced temperature, preferably between $-20°$ and $+10°$ C., into the corresponding mono-O-acyl-1.4;3.6-dianhydrohexitol which then, by the addition of an aqueous, for example 25% ammonia solution, or by the addition of a primary alkylamine with 1 to 4 C-atoms, possibly with the addition of a suitable solvent, is subjected to an aminolysis, namely, advantageously under increased pressure, preferably at a pressure of 2-20 ats., and elevated temperature, preferably at 90° to 180° C. The aminolysis is expediently carried out in a closed steel autoclave up to quantitative reaction. Suitable solvents are—possibly with the addition of water—e.g. alcohols, di- or polyglycol ethers or dioxan.

In the case of the aminolysis to the corresponding possibly N-monoalkyl-substituted aminodesoxy-1.4;3.6-dianhydrohexitol, the mesylate or tosylate group is exchanged for an amino or a monoalkylamino group with 1 to 4 C-atoms according to the reaction mechanism of a typical bimolecular nucleophilic substitution ($S_N2$ reaction), which always involves a reversal of the configuration on the central carbon atom. This reversal of configuration, which is also well known to the expert under the terms "inversion" or "Walden inversion", is the reason why, from the 1.4;3.6-dianhydro-D-glucitol-5-acyl derivative, in which the acyl radical is present in the 5-position endo-standing, there always results the 1.4;3.6-dianhydro-L-iditol derivative substituted in the 5-position by the amino group or a monoalkylamino group with 1 to 4 C-atoms, in which the substituent entering into the molecule in place of the acyl radical no longer stands in the endo- but rather in the exoposition. The Walden inversion involving the $S_N2$ reaction is, in completely corresponding manner, responsible for the fact that, from the corresponding iditol acylate, there always results the glucitol derivative endo-substituted in the 5-position, from the mannitol acylate the corresponding glucitol derivative exo-substituted in the 2-position and from the glucitol-2-exo-acylate the corresponding mannitol derivative endo-substituted in the 2-position.

The aminodesoxy-1.4;3.6-dianhydrohexitols resulting in the course of the hitherto described first synthesis route always display a free hydroxyl group in the 2- or 5-position of the 1.4;3.6-dianhydrohexitol ring system. This free hydroxyl group is esterified with nitric acid, nitrating acid or with a mixture of nitric acid and glacial acetic acid/acetic anhydride in the presence of urea to give the corresponding aminodesoxy-1.4;3.6-dianhydrohexitol mononitrate, whereby, instead of the free aminodesoxy-1.4;3.6-dianhydrohexitol, for the esterification there can also be used a suitable acid-addition salt, for example the corresponding salt with methanesulphonic acid, nitric acid or sulphuric acid.

The so resulting mononitrate is subsequently condensed with a reactive purine derivative, possibly in the presence of an adjuvant base, to give the desired compound according to the invention. Suitable purine derivatives are the N-(ω-haloalkyl)-, especially the N-(ω-bromoalkyl)-, N-(epoxyalkyl)- and N-(ω-acyloxyalkyl) derivatives of N',N"-dialkyl-substituted xanthines and the corresponding 9-N-derivatives of adenine. As ω-acyloxyalkyl derivatives, there are especially suitable the ω-methanesulphonyloxy or -p-toluenesulphonyloxyalkyl derivatives.

For the preparation of those compounds according to the invention in which the isohexide ring system is connected via a straight-chained, unsubstituted alkyl group with a ring nitrogen atom of the purine derivative, the corresponding aminodesoxy-1.4;3.6-dianhydrohexitol nitrate is preferably reacted with an N-(ω-bromo- or ω-methanesulphonyloxy-alkyl)-theophylline, -theobromine, -dialkylxanthine or -adenine, thus, for example with 7-(2-bromoethyl)-theophylline, 7-(3-bromopropyl)-theophylline, 7-(3-methanesulphonyloxypropyl)-theophylline, 7-(4-bromobutyl)-theophylline, 7-(5-bromopentyl)-theophylline, 7-(6-bromohexyl)-theophylline, 1-(3-bromopropyl)-theobromine, 3-isobutyl-1-methyl-7-(3-bromopropyl)-xanthine, 9-(2-bromoethyl)-adenine, 9-(3-bromopropyl)-adenine, 9-(4-bromobutyl)-adenine, 9-(5-bromopentyl)-adenine or 9-(6-bromohexyl)-adenine.

For the preparation of those compounds according to the invention in which the "bridge" between the aminoisohexide ring system and the purine derivative is formed by a hydroxyalkyl group, the corresponding aminodesoxy-1.4;3.6-dianhydrohexitole nitrate is reacted with an epoxyalkyl derivative of the desired purine base, for example with 7-(2,3-epoxypropyl)-theophylline.

For the preparation of those compounds according to the invention in which the "bridge" between the aminoisohexide and the purine derivative is an alkylene group, according to a further process according to the invention, one can transpose the two last-mentioned process steps in such a manner that one first reacts the corresponding aminoisohexide in the previously described manner with a reactive purine derivative, such as e.g. ω-bromo- or ω-methanesulphonyloxyalkyl derivative of theophylline, theobromine, N,N-dialkylated xanthines or of adenine, to give the corresponding purinylalkylaminoisohexide and this esterifies with nitric acid in the previously described way.

For the avoidance of disubstitution on the nitrogen of the aminoisohexide, the amine nitrogen of the aminoisohexide can, before the reaction with the reactive purine derivative, be provided ith a suitable protective group, e.g. the benzyl radical, which, after the reaction with the reactive purine derivative, can easily be split off again, e.g. by hydrogenation in the presence of a conventional noble metal catalyst.

A further suitable process for the preparation of those compounds according to the invention in which the "bridge" between the aminoisohexide and the purine derivative is an alkylene group, consists in that one subjects the corresponding aminoisohexide, together with an ω-acylalkyl- or ω-oxoalkyl-xanthine or -adenine derivative in per se known manner to a reductive condensation in the presence of hydrogen and a suitable noble metal or noble metal sulphide catalyst, possibly in the presence of a solvent. In the case of the ω-oxoalkylxanthine or -adenine derivatives, for example of 7-(3-oxopropyl)-theophylline, there result the corresponding purinylalkylaminoisohexide derivatives with unbranched alkylene bridge, e.g. 3-theophyllin-7-ylpropylaminoisohexide, the free hydroxyl group of which is esterified in the following reaction step in the previously described manner with nitric acid, nitrating acid or nitric acid/acetic anhydride/acetic acid to give the end product according to the invention, e.g. 3-theophyllin-7-ylpropylaminoisohexide nitrate.

In the case of the ω-acylalkyl-xanthine or -adenine derivatives, e.g. of 7-(2-acetylethyl)-theophylline or 7-(4-acetylbutyl)-theophylline, there result, in the case of the reductive condensation with the aminoisohexide and subsequent esterification with nitric acid, nitrating acid or nitric acid/acetic anhydride/acetic acid, those ω-purinylalkylaminoisohexide nitrates according to the invention in which the alkylene bridge is branched, such as e.g. in the case of 3-theophyllin-7-yl-1-methylpropylaminoisohexide nitrate or 5-theophyllin-7-yl-1-methylpentylaminoisohexide nitrate. The so obtained compounds according to the invention with branched alkylene bridge possess an additional centre of asymmetry so that, in each case, two diastereomers are obtained in the case of the reductive condensation. These can be separated either immediately or better after the esterification to the corresponding nitric acid esters with the help of the conventional methods of separation, e.g. by column chromatography, liquid-liquid partitioning or fractional crystallisation, into the two isomeric end products, e.g. (+)-5-(3-theophyllin-7-yl-1-methylpropylamino)-5-desoxy-1.4;3.6-dianhydro-L-iditol 2 nitrate and into the corresponding (−)-isomer.

The hitherto described first route according to the invention for the preparation of the compounds according to the invention, in which the corresponding isohexide is converted with a sulphonic acid chloride, preferably with methanesulphonic acid chloride or toluenesulphonic acid chloride, into the corresponding monoacyl-1.4;3.6-dianhydrohexitol, has the disadvantage that, in the case of the acylation, there results not only the corresponding 5-O-acyl derivative or 2-O-acyl derivative but also, at the same time, the 2,5-diacyl derivative, so that, in the case of the isoidide and isomannide derivatives, in each case, the monoacyl compound must be separated from the diacylate, whereas in the case of isosorbide, in which two stereoisomeric monoacyl derivatives result, besides the diacylate, the desired acylate must be isolated from the mixture of the three acyl derivatives. The separation of the acylate mixture takes place either by fractional crystallisation, fractional extraction or with the help of other per se known methods.

The laborious and time-consuming separation of the acylate mixture disappears, however, in the case of the use of the second synthesis route according to the invention to give the 5-purinylalkylaminoisoidide derivatives in that 1.4;3.6-dianhydro-D-glucitol is reacted quantitatively with an excess of sulphonic acid chloride, preferably methanesulphonyl chloride or toluenesulphonyl chloride, in pyridine or chloroform/triethylamine, to give the corresponding 1.4;3.6-dianhydro-D-glucitol 2,5-diacylate.

The diacylate is then, under the corresponding conditions such as described in the case of the first synthesis route, subjected to the ammonolysis, whereby, besides a small amount of 2,5-diamino-2,5-didesoxy-1.4;3.6-dianhydro-D-glucitol remaining in the aqueous phase, there results a mixture of 5-amino-5-desoxy-1.4;3.6-dianhydro-L-iditol and 5-amino-5-desoxy-1.4;3.6-dianhydro-L-iditol 2-methanesulphonate in the ratio of 1:4.

This 1:4 mixture is then subjected to an alkaline or acidic hydrolysis and the corresponding 5-amino-5-desoxy-1.4;3.6-dianhydro-L-iditol is subsequently, as described in the first synthesis route, esterified to the corresponding mononitrate and condensed with the desired purine derivative or first condensed with the desired purine derivative and subsequently esterified to the mononitrate.

As follows from the fact that the ammonolysis of the 2,5-diacylate leads preponderantly to the 5-amino-2-acylate, the nucleophilic substitution of the 2-exoacylate group in the isosorbide diacylate is sterically hindered. The degree of steric hindrance is temperature dependent. In order to obtain the 5-amino-2-acylate as quantitatively as possible from the corresponding diacylate, one works, therefore, according to the invention preferably at a temperature of 80° to 110° C. since at temperatures above 110° C. the exo-acyl group, even if only to a small extent, is attacked by ammonia or by the monoalkylamine used. As solubilising agent, an alcohol, preferably ethanol, can be added to the aqueous ammonia solution or to the monoalkylamine.

In the case of a further route according to the invention for the preparation of the compounds according to the invention, one makes use of the surprisingly discovered fact that 1.4;3.6-dianhydro-D-glucitol 2,5-diacylate (dimesylate or ditoylsate) is selectively attacked on the $C^5$-atom by sodium benzoate in a suitable solvent, preferably a dipolar aprotic solvent, for example in anhydrous dimethylformamide, dimethyl sulphoxide or diethers of ethylene glycol, at temperatures of 100° to 180° C., preferably of 120° to 150° C., so that, with reversal of configuration, 1.4;3.6-dianhydro-L-iditol 2-methanesulphonate 5-benzoate or 1.4;3.6-dianhydro-L-iditol 2-toluenesulphonate 5-benzoate result in high yield. This product is now again subjected to the ammonolysis with 25% ammonia solution or to the aminolysis under elevated pressure and elevated temperature, whereby the benzoic acid ester is split off hydrolytically, namely, surprisingly with maintenance of the configuration on the $C^5$-atom, whereas the acylate radical on the $C^2$-atom is, with reversal of configuration, substituted by the amino or alkylamino group to give the corresponding 5-amino-5-desoxy-1.4;3.6-dianhydro-D-glucitol or 5-alkylamino-5-desoxy-1.4;3.6-dianhydro-D-glucitol.

Since the last-mentioned elegant process involves a double selective reversal of configuration, the configuration of the end product is, with regard to its substituents, identical with the configuration of the starting compound; from the isosorbide disulphonate there again results an isosorbide derivative, namely, 5-amino- or 5-alkylamino-5-desoxy-1.4;3.6-dianhydro-D-glucitol.

The so obtained 5-amino-5-desoxy-1.4;3.6-dianhydro-D-glucitol derivatives can subsequently be condensed in a manner analogous to the previously described reaction routes with reactive purine derivatives to give the 5-(ω-purinylalkylamino)-5-desoxy-1.4;3.6-dianhydro-D-glucitol derivatives according to the invention, whereby the esterification with nitric acid can take place, depending upon the process variant, before or after the condensation.

In order to convert the compounds according to the invention into their physiologically acceptable salts, there can be used inorganic acids and mineral acids, such as hydrohalic acids, sulphuric acid or phosphoric acids, as well as organic acids, such as carboxylic and sulphonic acids, for example, malonic, succinic, lactic, tartaric, malic, benzoic, salicylic, citric, ascorbic, nicotinic or p-toluenesulphonic acid. The free bases can again be liberated from their acid-addition salts by treatment with strong bases, for example sodium or potassium hydroxide.

Furthermore, the subject of the invention are pharmaceutical compositions which, besides conventional carrier and additive materials, contain at least one of the compounds according to the invention or of their physiologically acceptable salts. These compositions can be used as medicaments in human and veterinary medicine. Conventional carrier materials are, for example, water, vegetable oils, polyethylene glycols, glycerol esters, gelatine, carbohydrates, such as lactose or starch, magnesium stearate, talc, Vaseline. Conventional additive materials are, for example, preserving, stabilising, lubricating, wetting agents, emulsifiers, physiologically acceptable salts, buffer substances, colouring, flavouring and aroma materials. The selection of the carrier and additive materials depends upon whether the compounds according to the invention are to be administered enterally, parenterally or topically.

The compounds according to the invention can also be administered in admixture with other active materials, for example vitamins or known commercially available heart-circulatory agents, especially also with β-receptor blockers.

EXAMPLE OF A PHARMACEUTICAL COMPOSITION

For the preparation of tablets each of 100 mg. individual weight, each of which contains 5 mg. of active material, one needs e.g.

I. 5 g. 5-(3-theophyllin-7-ylpropyl)-amino-5-desoxy-1.4;3.6-dianhydro-L-iditol 2-nitrate hydrochloride
II. 54 g. microcrystalline cellulose
III. 20 g. lactose
IV. 20 g. maize starch
V. 0.5 g. colloidal silicic acid
VI. 0.5 g. magnesium stearate.

The substances I–IV are dry mixed for 10 minutes, subsequently the mixture is added to the substances V and VI, one mixes for a further 10 minutes and presses the so obtained powder on a tabletting machine to give tablets of 100 mg. individual weight.

Each of the compounds and intermediate products according to the invention mentioned in the following Examples represents an especially suitable agent for the preparation of pharmaceutical compositions.

The abbreviations contained in the Examples have the following meanings:
m.p. = melting point (uncorrected)
(decomp.) = decomposition
d = density
$[\alpha]_D^{25}$ = optical rotation at 25° C., sodium D line.

After the optical rotational values are given the concentrations of the measured solutions, whereby c 2, for example, means a concentration of 2 g./100 ml. of solution; the solvent is, in each case, given separately.

All temperatures are given in °C.

EXAMPLE NO. 1

5-(3-Theophyllin-7-ylpropyl)-amino-5-desoxy-1.4;3.6-dianhydro-1-iditol 2-nitrate (a) 1.4;3.6-Dianhydro-D-glucitol 2-methanesulphonate, 5-methanesulphonate and 2,5-dimethanesulphonate To a solution of 4.82 kg. (33 mol) 1.4;3.6-dianhydro-D-glucitol in 24 liters pyridine one adds dropwise, with the exclusion of moisture, stirring and cooling to −15° to −20°, within the course of several hours, 3.1 liters (40 mol) methanesulphonic acid chloride. Subsequently, one further stirs for 15 hours without cooling. One distils off the pyridine in vacuo, adds the oily residue to 15 liters of water, boils up and allows to cool. Suction filtration, washing with 4 liters of water and drying of the crystalline precipitate gives 2.22 kg. (7.34 mol) 1.4;3.6-dianhydro-D-glucitol 2,5-dimethanesulphonate. The filtrate is neutralised, with stirring and water cooling, with about 1.5 kg. sodium hydroxide and evaporated to dryness at about 70°. The dry residue is hot extracted continuously with a total of 30 liters of chloroform and the extract is filtered hot. One leaves the extract to stand for 15 hours at 20°, filters off the crystalline precipitate with suction, washes it twice with 2 liter amounts of chloroform, dries and obtains 2.3 kg. (10.26 mol) 1.4;3.6-dianhydro-D-glucitol 5-methanesulphonate. The combined filtrates are evaporated in a vacuum and the residue dissolved hot in 22 liters of ethanol. One allows to stand for 15 hours at 20°, filters off the crystalline precipitate with suction, washes it twice with 3 liter amounts of ethanol, dries and obtains 0.65 kg. (2.90 mol) 1.4;3.6-dianhydro-D-glucitol-2-methanesulphonate. Evaporation of the filtrate gives 2.21 kg. (9.85 mol) of a mixture of the two isomeric monomethanesulphonates which, according to need, can be further separated by repetition of the alternating crystallisation from chloroform and ethanol, or by esterification with methanesulphonic acid chloride in pyridine, is completely converted into 1.4;3.6-dianhydro-D-glucitol 2,5-dimethanesulphonate.

Analytical amounts of the methanesulphonates give, after recrystallisation, correct elementary analysis and the melting points and optical rotations set out in Table 1:

TABLE 1

| 1.4; 3.6-dianhydro-D-glucitol- | recrystallised from | m.p. [°C.] | $[\alpha]_D^{25}$ |
|---|---|---|---|
| 2-methane-sulphonate | chloroform | 135–138.5 | 62.5 (c 2; acetone) |
| 5-methane-sulphonate | chloroform | 123–124 | 75.9 (c 2; methanol) |
| 2,5-dimethane-sulphonate | ethanol/acetone | 127–128 | 74 (c 2; acetone) |

Remark:
If one reacts 1.4; 3.6-dianhydro-D- glucitol with the 2 to 2.5 fold molar amount of methanesulphonic acid chloride under the same reaction conditions, one obtains 1.4; 3.6-dianhydro-D- glucitol 2,5-dimethanesulphonate in almost quantitative yield.

(b) 5-Amino-5-desoxy-1.4;3.6-dianhydro-L-iditol

This intermediate product can be obtained in 2 ways:

Process 1

Preparation by ammonolysis of 1.4;3.6-dianhydro-D-glucitol 5-methanesulphonate. A mixture of 448 g. (2 mol) 1.4;3.6-dianhydro-D-glucitol 5-methanesulphonate and 1.5 liter of 25% aqueous ammonia (20 mol) is stirred in a closed steel autoclave for 24 hours at 130°. Thereafter, the reaction is quantitative. One evaporates under reduced pressure and dries azeotropically by successive addition and renewed evaporation of 1 liter each of ethanol and chloroform. The oily residue is dissolved, with warming, in 500 ml. ethanol and diluted with isopropanol to 2 liters. Upon cooling, there crystallise out 311 g. (1.3 mol) 5-amino-5-desoxy-1.4;3.6-dianhydro-L-iditol as methanesulphonic acid salt. A further 100 g. (0.4 mol) of crystalline pure product precipitate out after treatment of the mother liquor with 30 g. active charcoal and concentration of the filtrate. For analysis, one recrystallises from ethanol/chloroform.

M.p. 151°–4°; $[\alpha]_D^{25}$ 27.6 (c 1; water)

Elementary analysis: $C_6H_{11}NO_3$ x $CH_3SO_3H$ (241.27): calc.: C (34.83), H (6.27), N (5.81). found: C (34.71), H (6.45), N (5.36).

A small portion of the product is converted into the free base and recrystallised from chloroform/ether. M.p. 103°–104°; $[\alpha]_D^{25}$ 31.6 (c 2; water).

Process 2

Ammonolysis of 1.4;3.6-dianhydro-D-glucitol 2,5-dimethanesulphonate, followed by alkaline hydrolysis of the 5-amino-5-desoxy-1.4;3.6-dianhydro-L-iditol 2-methanesulphonate obtained.

A mixture of 302 g. (1 mol) 1.4;3.6-dianhydro-D-glucitol-2,5-dimethanesulphonate, 750 ml. of 25% aqueous ammonia (10 mol) and 750 ml. ethanol is stirred in a closed steel autoclave for 4 days at 100°. After cooling, one mixes with 1 liter of water and filters off with suction from unreacted dimethanesulphonate which has crystallised out (106 g. = 0.35 mol). The filtrate is mixed with 104 g. (1.3 mol) sodium hydrogen carbonate for the removal of ammonia and evaporated under reduced pressure. One dissolves in 5 liters of water and extracts elimination products with 500 ml. chloroform. The aqueous phase is continuously extracted with chloroform for 48 hours in a rotary perforator (Normag). 2,5-Diamino-2,5-didesoxy-1.4;3.6-dianhydro-D-glucitol resulting as by-product remains in the aqueous phase. The chloroform extract, after drying over anhydrous sodium sulphate, filtering and evaporating, gives 105 g. (about 0.55 mol) of a 1:4 mixture of 5-amino-5-desoxy- 1.4;3.6-dianhydro-L-iditol and 5-amino-5-desoxy-1.4;3.6-dianhydro-L-iditol 2-methanesulphonate.

For the characterisation of the latter product, a small portion of the mixture is dissolved in chloroform, washed 2 times with water, the chloroform phase evaporated, converted into the methanesulphonic acid salt and recrystallised 2 times from ethanol.

M.p. 213°–5°; $[\alpha]_D^{25}$ 39.0 (c 0.50; water)

Elementary analysis: $C_7H_{13}NO_5S \times CH_3SO_3H$ (319.37): calc.: C (30.09), H (5.37), N (4.39), S (20.08). found: C (30.13), H (5.49), N (4.25), S (20.6).

The above-obtained mixture is added to a solution of 60 g. (1.5 mol) sodium hydroxide in 1.5 liters of water and boiled under reflux for 24 hours. After cooling, one adjusts to pH=10 by the addition of conc. hydrochloric acid, filters and evaporates under reduced pressure, then dries azeotropically with n-butanol, heats the residue with 500 ml. n-butanol and filters off from inorganic salts. The butanolic solution is evaporated, the residue is dissolved in 200 ml. isopropanol and mixed with 34 g. (0.35 mol) methanesulphonic acid. 80 g. (0.33 mol) 5-amino-5-desoxy-1.4;3.6-dianhydro-L-iditol crystallise out in the form of the methanesulphonic acid salt. M.p. 150°–2°.

Yield, referred to reacted 1.4;3.6-dianhydro-D-glucitol 2,5-dimethanesulphonate: 50%.

(c) 5-Amino-5-desoxy-1.4;3.6-dianhydro-L-iditol 2 nitrate 241 g. (1 mol) 5-Amino-5-desoxy-1.4;3.6-dianhydro-L-iditol hydrogen methanesulphonate (or 145 g. of the free base) are dissolved in 50 ml. of water and mixed, while cooling, dropwise with 30 ml. conc. sulphuric acid (d=1.84; 0.54 mol) (Solution A).

A solution of 14 g. (0.23 mol) urea in 300 ml. conc. sulphuric acid (d=1.84; 5.4 mol) is added dropwise, with stirring and cooling to −15°, to 200 ml. of 96% nitric acid (d=1.5; 4.5 mol). Subsequently, one adds Solution A thereto dropwise at −15° within 3–4 hrs. and further stirs at this temperature for 2 hrs. The reaction mixture is slowly stirred into 1.5 liters of water. While cooling, one neutralises by the slow addition of a solution of 630 g. (15.75 mol) of sodium hydroxide (or 590 g. NaOH if the free base has previously been used) in 2 liters of water and filters. The filtrate is continuously extracted with chloroform for 16 hours in a 5 liter rotary perforator. From the chloroform extract one obtains, after drying over anhydrous sodium sulphate, filtering and evaporating under reduced pressure, 158 g. (0.83 mol) 5-amino-5-desoxy-1.4;3.6-dianhydro-L-iditol 2-nitrate as a slowly crystallising oil. For characterisation, one converts a small portion into the hydrochloride and recrystallises from isopropanol.

M.p. 201°–208° (decomp.); $[\alpha]_D^{25}$ 54.1 (c 2; water)

Elementary analysis: $C_6H_{10}N_2O_5 \times HCl$ (226.62): calc.: C (31.80), H (4.89), N (12.36), Cl (15.64). found: C (31.78), H (4.92), N (12.20), Cl (15.6).

(d) 5-(3-Theophyllin-7-ylpropyl)-amino-5-desoxy-1.4;3.6-dianhydro-L-iditol 2-nitrate A mixture of 93 g. (0.49 mol) 5-amino-5-desoxy-1.4;3.6-dianhydro-L-iditol 2-nitrate and 500 ml. ethanol is placed in a 1 liter Soxhlet extractor and the extraction cup provided with 66 g. (0.22 mol) 7-(3-bromopropyl)-theophylline [preparation e.g. according to H. Priewe and A. Poljak, Chem. Ber., 90, 1651–5 (1957)]. One heats under reflux for 18 hrs, while stirring, whereby the contents of the cup have been completely extracted into the reaction mixture after about 3 hrs. After cooling, one adds 400 ml. chloroform thereto, filters off with suction from precipitated excess 5-amino-5-desoxy-1.4;3.6-dianhydro-L-iditol 2-nitrate hydrobromide and then washes with 200 ml. each of ethanol and chloroform. The filtrate is, after evaporation under reduced pressure, dissolved in 400 ml. chloroform, successively washed 2 times with 100 ml. amounts of water and with 100 ml. 1 molar aqueous sodium hydroxide solution, whereby residual 5-amino-5-desoxy-1.4;3.6-dianhydro-L-iditol 2-nitrate is removed, and subsequently extracted 9 times with 100 ml. amounts of 0.2 molar hydrochloric acid. The remaining chloroform phase and the hydrochloric acid phase No. 9 contain disubstitution product and are discarded. The hydrochloric acid phases Nos. 1–8 are evaporated under reduced pressure and recrystallised from ethanol/water. One obtains 61.4 g. (137 mmol) 5-(3-theophyllin-7-ylpropyl)-amino-5-desoxy-1.4;3.6-dianhydro-L-iditol 2-nitrate in the form of the hydrochloride.

M.p. 207°–8° (decomp.); $[\alpha]_D^{25}$ 29.4 (c 0.5; water)

Elementary analysis: $C_{16}H_{22}N_6O_7 \times HCl$ (446.85): calc.: C (43.01), H (5.19), N (18.81), Cl (7.93). found: C (42.98), H (5.35), N (18.40), Cl (8.5).

EXAMPLE NO. 2

5-(2-Theophyllin-7-ylethyl)-amino-5-desoxy-1.4;3.6-dianhydro-L-iditol 2-nitrate. Preparation analogous to Example No. 1 (d) by the reaction of excess 5-amino-5-desoxy-1.4;3.6-dianhydro-L-iditol 2-nitrate with 7-(2-bromoethyl)-theophylline. The product is isolated as hydrochloride and recrystallised from ethanol. Yield: 47%.

M.p. 166° (decomp.); $[\alpha]_D^{25}$ 36.8 (c 0.5; water)

Elementary analysis: $C_{15}H_{20}N_6O_7 \times HCl$ (432.83): calc.: C (41.63), H (4.89), N (19.42), Cl (8.19). found: C (41.30), H (5.01), N (19.21), Cl (8.1).

EXAMPLE NO. 3

5-(4-Theophyllin-7-ylbutyl)-amino-5-desoxy-1.4;3.6-dianhydro-L-iditol 2-nitrate. Preparation analogous to Example No. 1 (d) by the reaction of excess 5-amino-5-desoxy-1.4;3.6-dianhydro-L-iditol 2-nitrate with 7-(4-bromobutyl)-theophylline. The product is isolated as hydrochloride and recrystallised from ethanol/isopropanol. Yield: 41%.

M.p. 183° (decomp.); $[\alpha]_D^{25}$ 32.1 (c 0.5; water)

Elementary analysis: $C_{17}H_{24}N_6O_7 \times HCl$ (460.88): calc.: C (44.30), H (5.47), N (18.23), Cl (7.69). found: C (43.94), H (5.49), N (17.87), Cl (8.0).

EXAMPLE NO. 4

5-(5-Theophyllin-7-ylpentyl)-amino-5-desoxy-1.4;3.6-dianhydro-L-iditol 2-nitrate. Preparation analogous to Example No. 1 (d) by the reaction of excess 5-amino-5-desoxy-1.4;3.6-dianhydro-L-iditol 2-nitrate with 7-(5-bromopentyl)-theophylline. The product is isolated as hydrochloride and recrystallised from ethanol/isopropanol. Yield: 39%.

M.p. 191° (decomp.); $[\alpha]_D^{25}$ 31.7 (c 0.5; water)

Elementary analysis: $C_{18}H_{26}N_6O_7 \times HCl$ (474.91): calc.: C (45.52), H (5.73), N (17.40), Cl (7.46). found: C (45.86), H (5.86), N (17.67), Cl (7.6).

EXAMPLE NO. 5

5-(6-Theophyllin-7-ylhexyl)-amino-5-desoxy-1.4;3.6-dianhydro-L-iditol 2-nitrate. Preparation analogous to Example No. 1 (d) by the reaction of excess 5-amino-5-desoxy-1.4;3.6-dianhydro-L-iditol 2-nitrate with 7-(6-bromohexyl)-theophylline. The product is isolated as hydrochloride and recrystallised from ethanol/isopropanol. Yield: 42%.

M.p. 152°–154° (decomp.); $[\alpha]_D^{25}$ 33.5 (c 1; chloroform)

Elementary analysis: $C_{19}H_{28}N_6O_7 \times HCl$ (488.93): calc.: C (46.68), H (5.98), N (17.19), Cl (7.25). found: C (46.80), H (6.09), N (17.09), Cl (7.6).

EXAMPLE NO. 6

5-(2-Hydroxy-3-theophyllin-7-ylpropyl)-amino-5-desoxy-1.4;3.6-dianhydro-L-iditol 2-nitrate. A mixture of 1.9 g. (10 mmol) 5-amino-5-desoxy-1.4;3.6-dianhydro-L-iditol, 20 ml. of 96% ethanol and 1.65 g. (7 mmol) 7-(2.3-epoxypropyl)-theophylline [preparation e.g. according to C.A., 57, P 13777 f (1962)] is boiled under reflux for 20 hrs. and evaporated under reduced pressure. The residue is separated chromatographically over a column with 340 g. silica gel (70–230 mesh. Woelm) and methanol/chloroform 8/2 as elution agent. The fractions containing the reaction product (Rf=0.54; silica gel finished plate Merck F 254, chloroform/methanol 8/2) are combined and evaporated under reduced pressure. One obtains 2.3 g. (5.4 mmol) 5-(2-hydroxy-3-theophyllin-7-ylpropyl)-amino-5-desoxy-1.4;3.6-dianhydro-L-iditol 2-nitrate, which is converted into the hydrochloride and recrystallised from isopropanol/ethanol.

M.p. 195°–198° (decomp); $[\alpha]_D^{25}$ 24.4 (c 1; water)

Elementary analysis: $C_{16}H_{22}N_6O_8 \times HCl$ (462.85). calc.: C (41.74), H (5.01), N (18.16), Cl (7.66). found: C (41.74), H (5.07), N (18.06), Cl (7.7).

EXAMPLE NO. 7

5-[3-(3,7-Dimethylxanthin-1-yl)-propylamino]-5-desoxy-1.4;3.6-dianhydro-L-iditol 2-nitrate

(a) 1-(3-Hydroxypropyl)-theobromine

To a mixture of 36 g. (0.2 mol) theobromine, 25 ml. (0.3 mol) 3-chloro-1-propanol and 100 ml. water, one adds dropwise, within 2 hrs., with stirring and heating to reflux, a solution of 12 g. (0.3 mol) sodium hydroxide in 30 ml. of water and then boils for 2 hrs. After cooling, one filters, evaporates the filtrate under reduced pressure, boils out the residue 2 times with 100 ml. amounts of ethanol and hot filters. The crude product which crystallises out upon cooling the ethanol extract gives, after renewed recrystallisation from ethanol, 24.3 g. (0.1 mol) 1-(3-hydroxypropyl)-theobromine. M.p. 139°–140°.

(b) 1-(3-Bromopropyl)-theobromine

To a mixture of 16.7 g. (70 mmol) 1-(3-hydroxypropyl)-theobromine and 100 ml. chloroform, one slowly adds dropwise, with stirring and heating to reflux, 13 ml. (140 mmol) phosphorus tribromide and further stirs for 4 hrs. under reflux. The cooled reaction mixture is stirred into 200 ml. ice water. After separation of the chloroform phase, one extracts the aqueous phase 3 times with 50 ml. amounts of chloroform, washes the combined chloroform phases with 100 ml. of water, dries over anhydrous sodium sulphate, filters and evaporates. The residue (18.1 g.) gives, after recrystallisation from ethanol, 16.2 g. (54 mmol) 1-(3-bromopropyl)-theobromine. M.p. 142°–144°.

(c) 5-[3-(3,7-Dimethylxanthin-1-yl)-propylamino]-5-desoxy-1.4;3.6-dianhydro-L-iditol 2-nitrate A mixture of 9.0 g. (30 mmol) 1-(3-bromopropyl)-theobromine, 100 ml. ethanol and 14.3 g. (75 mmol) 5-amino-5-desoxy-1.4;3.6-dianhydro-L-iditol 2-nitrate (preparation see Example 1 c) is boiled under reflux for 24 hrs. After cooling, one filters off excess 5-amino-5-desoxy-1.4;3.6-dianhydro-L-iditol 2-nitrate precipitated out as hydrobromide (7.3 g.; 27 mmol) and evaporates the filtrate under reduced pressure. The residue is dissolved in 100 ml chloroform, freed from residual starting amine by washing with 5% acetic acid, subsequently washed acid-free with 2% aqueous sodium hydroxide solution and, after drying over anhydrous sodium sulphate, evaporated under reduced pressure. One obtains 9.56 g. (23.3 mmol) of crude product, which is converted into the hydrochloride with 24 mmol ethanolic hydrochloric acid. After evaporating, one recrystallises from ethanol and obtains 6.9 g. (15.1 mmol) 5-[3-(3,7-dimethylxanthin-1-yl)-propylamino]-5-desoxy-1.4;3.6-dianhydro-L-iditol 2-nitrate hydrochloride with ½ mole water of crystallisation.

M.p. 176°–180° (decomp.); $[\alpha]_D^{25}$ 28.9 (c 0.4; water)

Elementary analysis: $C_{16}H_{22}N_6O_7 \times HCl \times \frac{1}{2}H_2O$ (455.86): calc.: C (42.16), H (5.31), N (18.44), Cl (7.78). found: C (42.16), H (5.19), N (18.32), Cl (8.2).

EXAMPLE NO. 8

5-[3-(3-Isobutyl-1-methylxanthin-7-yl)-propylanino]-5-desoxy-1.4:3.6-dianhydro-L-iditol 2-nitrate

(a) 3-Isobutyl-1-methyl-7-(3-hydroxypropyl)-xanthine

To a mixture of 10 g. (45 mmol) 3-isobutyl-1-methylxanthine, 40 ml. water and 5.4 ml. (65 mmol) 3-chloro-1-propanol, one adds dropwise, within 2 hrs., a solution of 2.6 g. (65 mmol) sodium hydroxide in 10 ml. water, with stirring and heating to reflux and then further boils for 2 hrs. One leaves to stand overnight at room temperature, filters off with suction the product which has crystallised out and recrystallises from ethanol. One obtains 5.9 g. (21 mmol) 3-isobutyl-1-methyl-7-(3-hydroxypropyl)-xanthine. M.p. 135°–137°.

(b) 3-Isobutyl-1-methyl-7-(3-bromopropyl)-xanthine

To a mixture of 5.1 g. (18 mmol) 3-isobutyl-1-methyl-7-(3-hydroxypropyl)-xanthine and 80 ml. chloroform, one slowly adds dropwise, with stirring and heating to reflux, 3.7 ml. (40 mmol) phosphorus tribromide and further boils for 3 hrs. The cooled mixture is stirred into 100 ml. ice water, the chloroform phase is separated off and the aqueous phase is extracted 3 times with 30 ml. amounts of chloroform. The combined chloroform phases give, after washing with 50 ml. water, drying over anhydrous sodium sulphate, filtering and evaporating under reduced pressure, 6.0 g. (17.5 mmol) 3-isobutyl-1-methyl-7-(3-bromopropyl)-xanthine as a colourless oil which, without further purification, is used in the following reaction step.

(c) 5-[3-(3-Isobutyl-1-methylxanthin-7-yl)-propylamino]-5-desoxy-1.4;3.6-dianhydro-L-iditol 2-nitrate 5 g. (14.6 mmol) of the previously described 3-isobutyl-1-methyl-7-(3-bromopropyl)-xanthine, together with 6.9 g. (36 mmol) 5-amino-5-desoxy-1.4;3.6-dianhydro-L-iditol 2-nitrate and 50 ml. ethanol, are boiled under reflux for 24 hrs. After cooling, one filters off from excess 5-amino-5-desoxy-1.4;3.6-dianhydro-L-iditol 2-nitrate as hydrobromide (3.5 g.; 13 mmol), evaporates the filtrate under reduced pressure, dissolves the residue in 50 ml. chloroform, extracts starting product still present with 1 molar hydrochloric acid, washes acid-free with 1 molar aqueous sodium hydroxide solution and evaporates the chloroform solution under reduced pressure after drying over anhydrous sodium sulphate and filtering. One obtains 3.0 g. (6.6 mmol) 5-[3-(3-isobutyl-1-methylxanthin-7-yl)-propylamino]-5-desoxy-1.4:3.6-dianhydro-L-iditol 2-nitrate. This is dissolved in ethanol, converted into the hydrochloride by the addition of 6.6 mmol of hydrochloric acid, boiled up with 1 g. active charcoal, filtered, evaporated under reduced pressure and dried in a vacuum (1 mbar). The hydrochloride so obtained is amorphous and melts, with decomposition, at 165°–170° C.

$[\alpha]_D^{25}$ 29.0 (c 2; methanol) and $[\alpha]_D^{25}$ 23.4 (c 0.29; dimethylformamide).

Elementary analysis: $C_{19}H_{28}N_6O_7$ x HCl (488.90): calc.: C (46.68), H (5.98), N (17.19), Cl (7.25). found: C (46.51), H (6.05), N (16.31), Cl (8.1).

EXAMPLE NO. 9

5-[N-Methyl-N-(3-theophyllin-7-ylpropyl)-amino]-5-desoxy-1.4;3.6-dianhydro-L-iditol 2-nitrate (a) 5-Methylamino-5-desoxy-1.4;3.6-dianhydro-L-iditol A mixture of 22.4 g. (0.1 mol) 1.4;3.6-dianhydro-D-glucitol 5-methanesulphonate (preparation see Example 1 a), 31. g. (1 mol) methylamine and 150 ml. n-butanol is stirred in a closed steel autoclave for 15 hrs. at 150° under an atmosphere of nitrogen. After cooling, one adds thereto a solution of 4 g. (0.1 mol) sodium hydroxide in 200 ml. n-butanol, stirs up, precipitates out the sodium methanesulphonate formed with 600 ml. chloroform, filters and evaporates the filtrate under reduced pressure. The oily crude base so obtained is dissolved in 100 ml. isopropanol and converted into the hydrogen nitrate with 6.5 ml. 65% nitric acid. After evaporation under reduced pressure, one recrystallises from isopropanol and obtains 15.3 g. (68.9 mmol) 5-methyl-amino-5-desoxy-1.4;3.6-dianhydro-L-iditol hydrogen nitrate.

M.p. 108°–109°; $[\alpha]_D^{25}$ 41.8 (c 1.0; water)

Elementary analysis: $C_7H_{13}NO_3$ x $HNO_3$ (222.20): calc.: C (37.84), H (6.35), N (12.61). found: C (38.00), H (6.60), N (12.23).

(b) 2-Methylamino-5-desoxy-1.4;3.6-dianhydro-L-iditol 2-nitrate

With stirring and cooling to 10°, to a mixture of 90 ml. acetic acid, 2.3 g. (38 mmol) urea and 10.2 g. (46 mmol) 5-methylamino-5-desoxy-1.4;3.6-dianhydro-L-iditol hydrogen nitrate one adds dropwise a solution of 5.9 ml. (138 mmol) 95% nitric acid in 46 ml. acetic acid and subsequently also 46 ml. acetic anhydride. After stirring for a further 4 hrs. at 10°, one precipitates out the crystalline reaction product with ether/petroleum ether. The precipitate, dissolved in 200 ml. water, is neutralised by the addition of sodium hydrogen carbonate and the solution extracted 4 times with 150 ml. amounts of chloroform. The chloroform extracts are, after washing with 100 ml. water, drying over anhydrous sodium sulphate/sodium carbonate and filtering, evaporated under reduced pressure. The so obtained crude base is dissolved in 100 ml. ethanol, converted into the hydrochloride with 46 ml. 1 molar hydrochloric acid, again evaporated under reduced pressure and recrystallised twice from ethanol/isopropanol. One obtains 5.58 g. (23.2 mmol) 5-methylamino-5-desoxy-1.4;3.6-dianhydro-L-iditol 2-nitrate hydrochloride. M.p. 163°–166° (decomp.); $[\alpha]_D^{25}$ 49 (c 1.0; water)

Elementary analysis: $C_7H_{12}N_2O_5$ x HCl (240.64): calc.: C (34.94), H (5.44), N (11.64), Cl (14.73). found: C (35.00), H (5.57), N (11.92), Cl (14.8 ).

(c) 5-[N-Methyl-N-(3-theophyllin-7-ylpropyl)-amino]-5-desoxy-1.4;3.6-dianhydro-L-iditol 2-nitrate To a mixture of 100 ml. anhydrous dimethylformamide, 8.4 g. (61 mmol) anhydrous, finely powdered potassium carbonate and 5.9 g. (29 mmol) 5-methylamino-5-desoxy-1.4;3.6-dianhydro-L-iditol 2-nitrate, one adds dropwise, with stirring, exclusion of moisture and warming to 50°, a solution of 10 g. (33 mmol) 7-(3-bromopropyl)-theophylline in 60 ml. anhydrous dimethylformamide and then stirs for 4 days at 50°. One filters, washes the filter residue with 150 ml. dimethylformamide, dilutes the filtrate with 300 ml. water, extracts twice with 200 ml. amounts of chloroform, washes the chloroform extracts with 200 ml. water, dries them over anhydrous sodium sulphate, filters and passes in hydrogen chloride up to saturation. One precipitates out the crude product with ether which, after reprecipitation from chloroform/ethanol with ether and after recrystallisation from isopropanol, gives 11.31 g. 24.5 mmol 5-[N-methyl-N-(3-theophyllin-7-ylpropyl)-amino]-5-desoxy-1.4;3.6-dianhydro-L-iditol 2-nitrate hydrochloride.

M.p. 167°–169°; $[\alpha]_D^{25}$ 22.8 (c 1.0; ethanol)

Elementary analysis: $C_{17}H_{24}N_6O_7$ x HCl (460.88): calc.: C (44.30), H (5.47), N (18.23), Cl (7.69). found: C (44.42), H (5.66), N (17.18), Cl (7.6).

EXAMPLE NO. 10

5-(3-Theophyllin-7-ylpropyl)-amino-5-desoxy-1.4;3.6-dianhydro-D-glucitol 2-nitrate (a) 5-Amino-5-desoxy-1.4;3.6-dianhydro-D-glucitol This starting product can be obtained in two ways.

Process I

Preparation and ammonolysis of 1.4;3.6-dianhydro-L-iditol 2-methanesulphonate

A solution of 73 g. (480 mmol) 96% 1.4;3.6-dianhydro-L-iditol in 500 ml. anhydrous pyridine is, with the exclusion of moisture, stirring and cooling to −20°, mixed dropwise with 52 ml. (660 mmol of 98% methanesulphonyl chloride and then stirred for 15 hrs. at −20°. The pyridine is distilled off as far as possible under reduced pressure and the residue, after the addition of 500 ml. hot water, heated until it dissolves. Upon cooling, 47.6 g. (157 mmol) 1.4;3.6-dianhydro-L-iditol 2,5-dimethanesulphonate crystallise out, which is filtered off with suction and then washed twice with 100 ml. amounts of water. The combined filtrates are neutralised by the addition of sodium hydrogen carbonate (pH=7), evaporated under reduced pressure and dried. The powdered dried residue is boiled out twice with 400 ml. amounts of chloroform and filtered while still hot. After cooling of the filtrate, 1.4;3.6-dianhydro-L-iditol 2-methanesulphonate crystallises out. The mother liquor gives further monomethanesulphonate after concentration. In all, one obtains 51.5 g. (213 mmol) 1.4;3.6- dianhydro-L-iditol 2-methanesulphonate. For analysis, a small amount is recrystallised from methanol.

M.p. 124°–125°; $[\alpha]_D^{25}$ 33.7 (c 1.0; acetone)

Elementary analysis: $C_7H_{12}O_6S$ (224.24): calc.: C (37.50), H (5.40), S (14.30). found: C (37.58), H (5.53), S (14.0).

33.6 g: (150 mmol) of the so obtained 1.4;3.6-dianhydro-L-iditol 2-methanesulphonate, together with a solution of 17 g. (1 mol) ammonia in 250 ml. n-butanol, are heated in a closed steel autoclave for 3 days at 170°. After cooling, one filters off with suction ammonium methanesulphonate which has crystallised out and then washes with 100 ml. n-butanol. The filtrate is extracted twice with 200 ml. amounts of water. The combined aqueous extracts are washed with 200 ml. chloroform, evaporated to dryness and dried azeotropically with butanol. The dry residue is boiled with 50 ml. n-butanol, with the addition of 10 g. anhydrous sodium sulphate, hot filtered and the filtrate evaporated. The so obtained oily crude product is taken up in 50 ml. chloroform, filtered and evaporated. One obtains 14 g. (96 mmol) of slowly solidifying 5-amino-5-desoxy-1.4;3.6-dianhydro-D-glucitol. For characterisation, one converts a small amount of the product into the hydrochloride and recrystallises from isopropanol. Decomposition point: 240°; $[\alpha]_D^{25}$ 39.1 (c 1.0; water)

Elementary analysis: $C_6H_{11}NO_3 \times HCl$ (181.63): calc.: C (39.68), H (6.66), N (7.71), Cl (19.52). found: C (39.85), H (6.89), N (7.66), Cl (19.3 ).

Process II

Preparation and selective ammonolysis of 1.4;3.6-dianhydro-L-iditol 2-methanesulphonate 5-benzoate A mixture of 604 g. (2 mol) 1.4;3.6-dianhydro-D-glucitol 2,5-dimethanesulphonate, 317 g. (2.2 mol) sodium benzoate and 8 liters of anhydrous dimethylformamide is stirred for 2 days at 145° in a steel autoclave under a protective atmosphere of nitrogen. The dimethylformamide is distilled off under reduced pressure, the residue is taken up in 5 liters of chloroform, successively extracted with 2 liter amounts of 1 molar aqueous sodium hydroxide solution and water, the chloroform phase dried over anhydrous sodium sulphate, filtered and concentrated to a volume of 1500 ml. The crude product which crystallises upon leaving to stand, is filtered off with suction, dissolved with warming in 500 ml. acetone and the hot solution poured into 1000 ml. ethanol. Upon cooling, 273 g. (0.83 mol) 1.4;3.6-dianhydro-L-iditol 2-methanesulphonate 5-benzoate crystallise out. The mother liquor gives, after evaporating and recrystallising, a further 120 g. (0.37 mol) of product which is slightly contaminated by starting substance. The analytical sample, after recrystallisation from ethanol, has the m.p. 117° and $[\alpha]_D^{25}$ 76.6 (c 2; chloroform).

Elementary analysis: $C_{14}H_{16}O_7S$ (328.35): calc.: C (51.21), H (4.91), S (9.76). found: C (51.60), H (5.05), S (9.6 ).

328 g. (1 mol) of the so obtained 1.4;3.6-dianhydro-L-iditol 2-methanesulphonate 5-benzoate, together with 1 liter of ethanol and 1.5 liters of 25% aqueous ammonia, are stirred for 1 day at 130° in a closed steel autoclave. One evaporates under reduced pressure, dissolves the residue in 1 liter of water, adjusts to pH=1 by the addition of conc. hydrochloric acid and filters off the precipitate—consisting of benzoic acid and benzamide—with suction. The filtrate is, after washing twice with 500 ml. amounts of chloroform, brought to pH=8 by the addition of sodium hydrogen carbonate, again evaporated and the residue extracted with 2 liters of ethanol. The ethanol extract is, after evaporation, extracted with 2 liters of chloroform, the chloroform extract boiled up with 60 g. active charcoal, filtered and evaporated. The so obtained 105 g. of crude product gives, after fractional distillation at 0.2 mm.Hg and 136°–142° pass-over temperature, 86.3 g. (0.59 mol) 5-amino-5-desoxy-1.4;3.6-dianhydro-D-glucitol.

(b) 5-Amino-5-desoxy-1.4;3.6-dianhydro-D-glucitol 2-nitrate 55 g. (0.38 mol) of the 5-amino-5-desoxy-1.4;3.6-dianhydro-D-glucitol obtained according to Process I or II are liquified by mixing with 3.5 ml. chloroform and this solution added dropwise, with stirring, to a solution, cooled to −15°, of 14 g. (0.23 mol) urea in 202 ml. (4.6 mol) 96% nitric acid (d=1.5). One further stirs for 15 hrs. at −15°, dilutes with 750 ml. of water and neutralises, while cooling, with a solution of 168 g. (4.2 mol) sodium hydroxide in 1.5 liters of water. One adjusts to pH=8 with sodium hydrogen carbonate, filters and continuously extracts the aqueous solution for 16 hrs. with chloroform in a 5 l. rotary perforator (Normag). The chloroform extract, after drying over anhydrous sodium sulphate and filtering, is evaporated under reduced pressure. The residue is dissolved in 200 ml. dichloromethane, freed from inorganic impurities by filtration and again evaporated under reduced pressure. One obtains 53 g. (0.28 mol) 5-amino-5-desoxy-1.4;3.6-dianhydro-D-glucitol 2-nitrate as a pale yellowish oil. For characterisation, one converts a small portion into the hydrochloride and recrystallises from ethanol/chloroform/petroleum ether.

M.p. 170°–171° (decomp.); $[\alpha]_D^{25}$ 50.7 (c 0.53; water)

Elementary analysis: $C_6H_{10}N_2O_5 \times HCl$ (226.62): calc.: C (31.80), H (4.89), N (12.36), Cl (15.64). found: C (32.00), H (5.10), N (12.14), Cl (15.6).

(c) 5-(3-Theophyllin 7-ylpropyl)-amino-5-desoxy-1.4;3.6-dianhydro-D-glucitol 2-nitrate To a boiling solution of 19 g. (100 mmol) 5-amino-5-desoxy-1.4;3.6-dianhydro-D-glucitol 2-nitrate in 150 ml. ethanol, one adds, via a Soxhlet cup, 12 g. (40 mmol) 7-(3-bromopropyl)-theophylline within 6 hrs. and heats under reflux for a further 14 hrs. One evaporates under reduced pressure and successively extracts the solution of the residue in 80 ml. chloroform twice with 40 ml. amounts of water and twice with 40 ml. amounts of 0.5 molar hydrochloric acid. The hydrochloric acid extracts are brought to pH=9 with 1 molar aqueous sodium hydroxide solution and re-extracted with chloroform. The chloroform extracts give, after drying over anhydrous sodium sulphate, filtering and evaporating under reduced pressure, 10.7 g. (26 mmol) of crude base which is dissolved in isopropanol and, by the addition of 27 ml. 1 molar hydrochloric acid, converted into the hydrochloride. Renewed evaporation under reduced pressure and two recrystallisations from isopropanol give 6.11 g. (12.8 mmol) 5-(3-theophyllin-7-ylpropyl)-amino-5-desoxy-1.4;3.6-dianhydro-D-glucitol 2-nitrate hydrochloride with ½ mole isopropanol of crystallisation (after drying at 70°, 1 mm.Hg).

M.p. 110° (after sintering from 86°); $[\alpha]_D^{25}$ 31.9 (c 0.5; water)

Elementary analysis: $C_{16}H_{22}N_6O_7 \times HCl \times \frac{1}{2} C_3H_8O$ (476.91): calc.: C (44.08), H (5.71), N (17.62), Cl (7.43). found: C (43.91), H (5.69), N (16.95), Cl (7.8).

EXAMPLE NO. 11

2-(3-Theophyllin-7-ylpropyl)-amino-2-desoxy-1.4;3.6-dianhydro-D-glucitol 5-nitrate (a) 1.4;3.6-Dianhydro-D-mannitol 2-methanesulphonate To a solution of 877 g. (6 mol) 1.4;3.6-dianhydro-D-mannitol in 6 liters of pyridine one adds dropwise, with stirring and the exclusion of moisture, as well as cooling to −15°, within 6 hrs., 525 ml. (6.6 mol) methanesulphonyl chloride, stirs for a further 3 days at −15° and then distils off the pyridine under reduced pressure. Upon mixing the oily residue with 2.7 liters of water, pure 1.4;3.6-dianhydro-D-mannitol 2,5-dimethanesulphonate crystallises out, which is separated off and washed 2 times with 700 ml. amounts of water. The combined filtrates are mixed with a solution of 264 g. (6.6 mol) sodium hydroxide in 2.5 liters of water, adjusted to pH=7 by the addition of sodium hydrogen carbonate, evaporated under reduced pressure and dried azeotropically with chloroform. The residue is hot extracted twice with 2.5 liter amounts of chloroform and filtered. The combined chloroform extracts are extracted 5 times with 1 liter amounts of water. Upon concentration of the aqueous phases, 1.4;3.6-dianhydro-D-mannitol 2-methanesulphonate crystallises out. The mother liquor remaining after the suction filtration gives further product after evaporation and recrystallisation from ethanol. Residual product is obtained by evaporation of the ethanolic mother liquor, dissolving the residue in water and continuous extraction of the aqueous solution with chloroform in a rotary perforator. Unreacted 1.4;3.6-dianhydro-D-mannitol remains in the aqueous phase. In all, one obtains 396 g. (1.77 mol) 1.4;3.6-dianhydro-D-mannitol 2-methanesulphonate (besides 465 g.=1.54 mol of the dimethanesulphonate). The analytical sample has, after recrystallisation from chloroform, the m.p. 111°–112° and $[\alpha]_D^{25}$ 118 c (1.0; acetone).

Elementary analysis: $C_7H_{12}O_6S$ (224.24): calc.: C (37.50), H (5.40), S (14.30). found: C (37.41), H (5.59), S (13.7).

(b) 2-Amino-2-desoxy-1.4;3.6-dianhydro-D-glucitol

A mixture of 224 g. (1 mol) of the previously obtained 1.4;3.6-dianhydro-D-mannitol 2-methanesulphonate and 1 liter of 25% aqueous ammonia is stirred for 24 hrs. at 120° in a closed steel autoclave. After cooling, one adds thereto 84 g. (1 mol) sodium hydrogen carbonate, evaporates under reduced pressure and boils out the residue with 2 liters of n-butanol. The evaporated butanol extract is taken up in 1 liter of chloroform, residual sodium methanesulphonate is filtered off and the filtrate evaporated. One obtains 130 g. (0.9 mol) 2-amino-2-desoxy-1.4;3.6-dianhydro-D glucitol as a pale yellowish oil. For characterisation one converts a small portion into the hydrochloride and recrystallises from isopropanol/methanol/chloroform.

M.p. 230° (decomp.); $[\alpha]_D^{25}$ 52.1 (c 1.0; water)

Elementary analysis: $C_6H_{11}NO_3 \times HCl$ (181.62): calc.: C (39.68), H (6.68), N (7.71), Cl (19.52). found: C (39.59), H (6.89), H (7.52), Cl (19.3 ).

(c) 2-Amino-2-desoxy-1.4;3.6-dianhydro-D-glucitol 5-nitrate

With stirring and cooling to −15°, to 200 ml. (4.5 mol 96% nitric acid (d=1.5), one first adds dropwise a solution of 14 g. 0.24 mol urea in 300 ml. (5.4 mol) sulphuric acid (d=1.84) and subsequently, within 4 hrs., a solution of 145 g. (1 mol) 2-amino-2-desoxy-1.4;3.6-dianhydro-D-glucitol in 50 ml. water and then stirs for 2 hrs. at −15°. One then stirs into 1.5 liters of water, adjusts, with cooling, to pH=8 to 9 by the gradual addition of 570 g. (14.3 mol) sodium hydroxide—dissolved in 2 liters of water—filters off sodium sulphate which has crystallised out, washes lipophilic by-products therefrom with 500 ml. chloroform and continuously extracts with chloroform for 16 hrs. in a rotary perforator. The chloroform extract gives, after drying over anhydrous sodium sulphate, filtering and evaporating under reduced pressure, 152 g. (0.8 mol) 2-amino-2-desoxy-1.4;3.6-dianhydro-D-glucitol 5-nitrate as a slowly solidifying oil. For characterisation, a small portion is converted into the hydrochloride and recrystallised from isopropanol/ethanol.

M.p. 181°–182° (decomp.); $[\alpha]_D^{25}$ 130 (c 0.52; water)

Elementary analysis: $C_6H_{10}N_2O_5 \times HCl$ (226.62): calc.: C (31.80), H (4.89), N (12.36), Cl (15.64). found: C (31.95), H (4.90), N (12.18), Cl (15.9).

(d) 2-(3-Theophyllin-7-ylpropyl)-amino-2-desoxy-1.4;3.6-dianhydro-D-glucitol 5-nitrate A mixture of 12 g. (40 mmol) 7-(3-bromopropyl)-theophylline, 19 g. (100 mmol) of the previously described 2-amino-2-desoxy-1.4;3.6-dianhydro-D-glucitol 5-nitrate and 100 ml. ethanol is boiled under reflux for 24 hrs. and subsequently evaporated under reduced pressure. One takes up in 80 ml. chloroform, washes 2 times with 40 ml. amounts of water and extracts 3 times with 50 ml. amounts of 0.5 molar hydrochloric acid. The hydrochloric acid extracts are adjusted to pH=8 to 9 with dilute aqueous sodium hydroxide solution, extracted several times with chloroform and the chloroform extracts, after drying with anhydrous sodium sulphate and filtering, are evaporated under reduced pressure. One obtains 22 g. of crude product which is dissolved in 200 ml. ethanol and converted into the hydrochloride by the addition of 50 ml. 1 molar hydrochloric acid. One again evaporates under reduced pressure, recrystallises twice from methanol and obtains 12.5 g. (28 mmol) 2-(3-theophyllin-7-ylpropyl)amino-2-desoxy-1.4;3.6-dianhydro-D-glucitol 5-nitrate hydrochloride.

M.p. 196°–201° (decomp.); $[\alpha]_D^{25}$ 72.6 (c 0.41; water)

Elementary analysis: $C_{16}H_{22}N_6O_7 \times HCl$ (446.86): calc.: C (43.01), H (5.19), N (18.81), Cl (7.93). found: C (42.70), H (5.13), N (18.75), Cl (8.4).

EXAMPLE NO. 12

5-(3-Theophyllin-7-ylpropyl)-amino-5-desoxy-1.4;3.6-dianhydro-D-mannitol 2-nitrate (a) 2-Amino-2-desoxy-1.4;3.6-dianhydro-D-mannitol A mixture of 448 g. (2 mol) 1.4;3.6-dianhydro-D-glucitol 2-methanesulphonate (preparation see Example 1a) and 1500 ml. of 25% aqueous ammonia is stirred for 1 day at 130° in a closed steel autoclave. After cooling, one adds 30 g. active charcoal thereto, filters and extracts with 1 liter of chloroform the 1.4;2.5;3.6-trianhydro-D-mannitol formed as by-product [after evaporation of the chloroform phase and recrystallisation from ether/petroleum ether a total of 104 g. (0.81 mol)]. The aqueous phase is, after evaporation under reduced pressure and azeotropic drying with ethanol and chloroform, extracted at boiling temperature with 2 liters of isopropanol. Upon concentrating the isopropanol extract to 0.5 liter, ammonium methanesulphonate which crystallises out is filtered off, the filtrate is neutralised with dilute sodium hydroxide solution, evaporated and extracted hot with 1 liter of n-butanol. The butanol extract is evaporated and the residue extracted with 1 liter of chloroform. Evaporation of the filtered chloroform extract gives 60 g. (0.41 mol) of oily crude base, which is dissolved in 100 ml. acetic acid and mixed dropwise with a solution of 15 ml. 96% nitric acid (d=1.5) in 75 ml. acetic acid. The hydrogen nitrate which crystallises out is filtered off with suction and recrystallised from isopropanol/ethanol. One obtains 32 g. (154 mmol) 2-amino-2-desoxy-1.4;3.6-dianhydro-D-mannitol hydrogen nitrate.

M.p. 192°–193° (decomp.); $[\alpha]_D^{25}$ 63.4 (c 0.51; water)
Elementary analysis: $C_6H_{11}NO_3$ x $HNO_3$ (208.18): calc.: C (34.62), H (5.81), N (13.45). found: C (34.52), H (5.97), N (13.55).

(b) 5-Amino-5-desoxy-1.4;3.6-dianhydro-D-mannitol 2-nitrate

To 60 ml. (1.35 mol) 96% nitric acid (d=1.5), one adds dropwise, with stirring and cooling to −15°, a solution of 4.2 g. (70 mmol) urea in 90 ml. (1.6 mol) sulphuric acid (d=1.84). At the same temperature, one slowly adds dropwise a solution of 21.8 g. (150 mmol) 2-amino-2-desoxy-1.4;3.6-dianhydro-D-mannitol (prepared from the previously obtained hydrogen nitrate) in 15 ml. water, then stirs for 2 hrs. at −15°, pours the reaction mixture into 1 liter of water, with stirring, and adjusts to pH=9 by the slow addition of 175 g. (4.38 mol) sodium hydroxide—dissolved in 1 l. water. Subsequently, one extracts continuously with chloroform for 8 hrs. in a rotary perforator. The chloroform extract gives, after drying over anhydrous sodium sulphate, filtering and evaporating under reduced pressure, 18.8 g. (99 mmol) 5-amino-5-desoxy-1.4;3.6-dianhydro-D-mannitol 2-nitrate as a slowly crystallising oil. For characterisation, one converts a small portion into the hydrochloride and recrystallises from ethanol.

M.p. 172° (decomp.); $[\alpha]_D^{25}$ 170.9 (c 0.5; water)
Elementary analysis: $C_6H_{10}N_2O_5$ x HCl (226.62): calc.: C (31.80), H (4.89), N (12.36), Cl (15.64). found: C (31.76), H (4.93), N (12.67), Cl (16.0).

(c) 5-(3-Theophyllin-7-ylpropyl)-amino-5-desoxy-1.4;3.6-dianhydro-D-mannitol 2-nitrate To a solution of 9.5 g. (50 mmol) of the previously obtained 5-amino-5-desoxy-1.4;3.6-dianhydro-D-mannitol 2-nitrate in 100 ml. ethanol, boiling under reflux, one extractively adds, via a Soxhlet cup, 6.0 g. (20 mmol) 7-(3-bromopropyl)-theophylline, further boils under reflux for 20 hrs., evaporates under reduced pressure, takes up the residue in 100 ml. chloroform and successively extracts 2 times with 100 ml. amounts of water, once with 30 ml. 0.3 molar acetic acid and 4 times with 50 ml. amounts of 0.1 molar hydrochloric acid. The hydrochloric extracts are adjusted to pH=9 with dilute aqueous sodium hydroxide solution, extracted several times with chloroform and the chloroform extracts combined, dried over anhydrous sodium sulphate, filtered and evaporated under reduced pressure. One obtains 7 g. (17 mmol) of crude base. For the separation of disubstitution product, one filters column chromatographically over 500 g. silica gel (Woelm 63–200), with chloroform/methanol 95/5 as eluent, evaporates the fractions with Rf=0.26 (silica gel; chloroform/methanol 9/1) and obtains 2.18 g. (5.3 mmol) pure 5-(3-theophyllin-7-ylpropylamino)-5-desoxy-1.4;3.6-dianhydro-D-mannitol 2-nitrate, which is dissolved in isopropanol, mixed with 5.3 ml. 1 molar hydrochloric acid, again evaporated and reprecipitated twice from chloroform with ether, which gives the hydrochloride.

M.p. 138°–143° (decomp.); $[\alpha]_D^{25}$ 118.3 (c 0.41; water)
Elementary analysis: $C_{16}H_{22}N_6O_7$ x HCl (446.85): calc.: C (43.01), H (5.19), N (18.81), Cl (7.93). found: C (42.97), H (5.27), N (18.71), Cl (8.2).

EXAMPLE NO. 13

5-(2-Adenin-9-ylethyl)-amino-5-desoxy-1.4;3.6-dianhydro-L-iditol 2-nitrate

A mixture of 7.3 g. (30 mmol) 9-(2-bromoethyl)-adenine (prepared by the reaction of adenine sodium salt with excess 1,2-dibromoethane), 70 ml. ethanol and 14.3 g. (75 mmol) 5-amino-5-desoxy-1.4;3.6-dianhydro-L-iditol 2-nitrate is boiled under reflux for 30 hrs. After cooling, one filters, evaporates the filtrate under reduced pressure, takes up the residue in 50 ml. chloroform, washes with 30 ml. water and extracts 3 times with 50 ml. amounts of 0.2 molar hydrochloric acid. The hydrochloric acid extracts are adjusted to pH=9 with dilute aqueous sodium hydroxide solution and extracted several times with chloroform. The combined chloroform extracts give, after drying over anhydrous sodium sulphate, filtering and evaporating under pressure, 10 g. (28 mmol) of crude product which is dissolved in 50 ml. ethanol and converted into the dihydrochloride by the addition of 60 ml. 1 molar hydrochloric acid. One again evaporates, recrystallises twice from isopropanol/water and obtains 5.44 g. (12 mmol) 5-(2-adenin-9-ylethyl)-amino-1.4;3.6-dianhydro-L-iditol 2-nitrate as dihydrochloride with 2 mols water of crystallisation.

M.p. 207°–209° (decomp.); $[\alpha]_D^{25}$ 52.4 (c 0.4; water)
Elementary analysis: $C_{13}H_{17}N_7O_5$ x 2 HCl x 2 $H_2O$ (460.28): calc.: C (33.92), H (5.04), N (21.30), Cl (15.41). found: C (33.94), H (4.92), N (21.24), Cl (16.4).

EXAMPLE NO. 14

5-(3-Adenin-9-ylpropyl)-amino-5-desoxy-1.4;3.6-dianhydro-L-iditol 2-nitrate is prepared analogously to Example 13 by the reaction of 9-(3-bromopropyl)-adenine with the 2.5 fold excess of 5-amino-5-desoxy-1.4;3.6-dianhydro-L-iditol 2-nitrate in boiling ethanol. The so obtained crude base is converted into the hydrochloride with the equimolar amount of hydrochloric acid and recrystallised from methanol.

M.p. 182°–183° (decomp.); $[\alpha]_D^{25}$ 42.7 (c 1; water)
Elementary analysis: $C_{14}H_{19}N_7O_5$ x HCl (401.82): calc.: C (41.85), H (5.02), N (24.40), Cl (8.82). found: C (41.41), H (4.96), N (24.10), Cl (8.8).

EXAMPLE NO. 15

5-(4-Adenin-9-ylbutyl)-amino-5-desoxy-1.4;3.6-dianhydro-L-iditol 2-nitrate is prepared analogously to Example 13 by the reaction of 9-(4-bromobutyl)-adenine with excess 5-amino-5-desoxy-1.4;3.6-dianhydro-L-iditol 2-nitrate in boiling ethanol. The crude base is converted into the dihydrochloride with the twofold molar amount of aqueous hydrochloric acid, evaporated and recrystallised from n-propanol. The dihydrochloride contains, in the crystal lattice, 1 mol $H_2O$ and 1 mol n-propanol (drying in a vacuum desiccator at room temperature). Above 75°, the substance gradually gives off water of crystallisation and propanol and decomposes at 150°.

$[\alpha]_D^{25}$ 27.8 (c 0.23; water).

Elementary analysis: $C_{15}H_{21}N_7O_5$ x 2 HCl x $H_2O$ x $C_3H_7OH$ (530.42): calc.: C (40.76), H (6.27), N (18.49), Cl (13.37). found: C (40.74), H (6.17), N (18.04), Cl (13.6).

EXAMPLE NO. 16

5-(5-Adenin-9-ylpentyl)-amino-5-desoxy-1.4;3.6-dianhydro-L-iditol 2-nitrate is prepared analogously to Example 13 by the reaction of 9-(5-bromopentyl)-adenine with excess 5-amino-5-desoxy-1.4;3.6-dianhydro-L-iditol 2-nitrate in boiling ethanol. The crude base is converted into the dihydrochloride with the 2 fold molar amount of hydrochloric acid and recrystallised twice from ethanol/isopropanol. After drying at 110°, the hemihydrate is obtained.

M.p. 202°–205° (decomp.); $[\alpha]_D^{25}$ 33.8 (c 0.4; water)

Elementary analysis: $C_{16}H_{23}N_7O_5$ x HCl x ½ $H_2O$ (475.35): calc.: C (40.43), H (5.51), N (20.63), Cl (14.92). found: C (40.72), H (5.62), N (20.51), Cl (14.7).

Drying at 140° gives the anhydrous dihydrochloride.

Elementary analysis: $C_{16}H_{23}N_7O_5$ x 2 HCl (466.34): calc.: C (41.21), H (5.40), N (21.03). found: C (41.69), H (5.50), N (21.08).

EXAMPLE NO. 17

5-(6-Adenin-9-ylhexyl)-amino-5-desoxy-1.4;3.6-dianhydro-L-iditol 2-nitrate is prepared analogously to Example 13 by the reaction of 9-(6-bromohexyl)-adenine with excess 5-amino-5-desoxy-1.4;3.6-dianhydro-L-iditol 2-nitrate in boiling ethanol. The crude base is converted into the dihydrochloride with the two fold molar amount of hydrochloric acid and recrystallised 2 times from ethanol/isopropanol.

M.p. 222° (decomp.); $[\alpha]_D^{25}$ 31.1 (c 0.4; water)

Elementary analysis (after drying at 140°): $C_{17}H_{25}N_7O_5$ x 2 HCl (480.37): calc.: C (42.51), H (5.67), N (20.41), Cl (14.76). found: C (42.69), H (5.76), N (20.38), Cl (14.4).

EXAMPLE NO. 18

(+)- and (−)-5-[1-methyl-3-(theophyllin-7-yl)-propylamino]-5-desoxy-1.4;3.6-dianhydro-L-iditol 2-nitrate (a)
(±)-5-[1-Methyl-3-(theophyllin-7-yl)-propylamino]-5-desoxy-1.4;3.6-dianhydro-L-iditol (diastereomeric mixture)

To a solution of 10 g. (40 mmol) 7-(3-oxobutyl)-theophylline in 75 ml. ethanol, one adds a solution of 5.8 g. (40 mmol) 5-amino-5-desoxy-1.4;3.6-dianhydro-L-iditol in 40 ml. methanol, adds thereto a suspension of 1.5 g. 10% Pd/C catalyst in 100 ml. ethanol, flushes with nitrogen and hydrogenates in a closed autoclave under 50 ats. hydrogen pressure for 20 hrs. at room temperature and for 8 hrs. at 50°. After cooling, decompressing and filtering off the catalyst, one evaporates the filtrate under reduced pressure, adjusts a solution of the residue in water to pH=2 with hydrochloric acid and percolates for 8 hrs. in a rotary percolator with chloroform in order to remove by-products. One adjusts the aqueous phase to pH=4 and again percolates with chloroform. Both chloroform phases are discarded. After adjustment to pH=7, one percolates for 8 hrs. with chloroform. From this chloroform phase one obtains, after drying over anhydrous sodium sulphate and evaporating under reduced pressure, 8.5 g. (22.4 mol) of reaction product which consists of a mixture of the two possible diastereomers. The mixture is, without further separation, used for the following esterification with nitric acid.

For analysis, a small portion is converted into the hydrochloride and recrystallised from isopropanol/pentane.

M.p. 155°–166° (decomp.); $[\alpha]_D^{25}$ 6.7 (c 0.39; water)

Elementary analysis: $C_{17}H_{25}N_5O_5$ x HCl (415.88): calc.: C (49.10), H (6.30), N (16.84), Cl (8.52). found: C (49.11), H (6.48), N (16.28), Cl (8.5).

(b) (+)- and (−)-5-1[-methyl-3-(theophyllin-7-yl)-propylamino]-5-desoxy-1.4;3.6-dianhydro-L-iditol 2-nitrate To a solution of 3 g. (50 mmol) urea in 40 ml. of 96% nitric acid (d=1.5; about 0.9 mol) one adds dropwise, with stirring and cooling to −20°, a solution of 8 g. (21 mmol) of the previously obtained diastereomer mixture in 20 ml. methanesulphonic acid and then stirs for 1 hr. at −20°. The mixture is stirred into 220 ml. ice water; to this is added dropwise a solution of 56 g. (1.4 mol) sodium hydroxide in 150 ml. water and the neutralisation is completed by the addition of sodium hydrogen carbonate. One extracts 5 times with 100 ml. amounts of chloroform, washes the chloroform phases with 100 ml. water, dries over anhydrous sodium sulphate, evaporates under reduced pressure and obtains 7 g. (16.5 mmol) of crude base (diastereomer mixture). This is separated column chromatographically over 200 g. silica gel with chloroform/methanol 95/5 as eluent. One obtains 3 fractions:

F 1: 2.24 g. (5.28 mmol) of free base with Rf=0.56 (silica gel; chloroform/methanol 9/1). Conversion into the hydrochloride and recrystallisation from ethanol give 1.3 g. (2.8 mmol) of the laevorotary diastereomer (−)-5-[1-methyl-3-(theophyllin-7-yl)-propylamino]-5-desoxy-1.4;3.6-dianhydro-L-iditol 2-nitrate hydrochloride of m.p. 201°–202° (decomp.) and $[\alpha]_D^{25}$ −13 (c 0.2; water)

Elementary analysis: $C_{17}H_{24}N_6O_7$ x HCl (460.88): calc: C (44.30), H (5.47), N (18.23), Cl (7.69). found: C (44.02), H (5.51), N (18.39), Cl (7.8).

Intermediate fraction: 3.3 g. (7.7 mmol) diastereomer mixture

F 2: 0.6 g. (1.4 mmol) of free base with Rf=0.51 (silica gel; chloroform/methanol 9/1). Conversion into the hydrochloride and recrystallisation from ethyl acetate and subsequently from isopropanol gives the dextrorotary diastereomer (+)-5-[1-methyl-3-(theophyllin-7-yl)-propylamino]-5-desoxy-1.4;3.6-dianhydro-L-iditol 2-nitrate hydrochloride of m.p. 158°–161° and $[\alpha]_D^{25}$ +34.8 (c 0.4; water).

Elementary analysis: $C_{17}H_{24}N_6O_7$ x HCl (460.88): calc.: C (44.30), H (5.47), N (18.23), Cl (7.69). found: C (44.26), H (5.61), N (18.21), Cl (7.8).

EXAMPLE NO. 19

5-(3-Theophyllin-7-ylpropylamino)-5-desoxy-1.4;3.6-dianhydro-L-iditol 2-nitrate (a) 7-(3-Methanesulphonyloxypropyl)-theophylline To a suspension of 1190 g. (5 mol) 7-(3-hydroxypropyl)-theophylline in 6500 ml. water- and ethanol-free chloroform are added 1110 ml. (8 mol) triethylamine and to this, with stirring, exclusion of moisture and cooling to −15°, are added dropwise 580 ml. (7.5 mol) methanesulphonyl chloride. One stirs for 1 hr. at −15°, allows to come to 20° and stirs the mixture into 2 liters of ice water. The chloroform phase is separated off, washed 3 times with 2 liters of water and once with 2 liters of aqueous sodium hydrogen carbonate solution. The combined wash liquids are re-extracted with 2 liters chloroform. The two chloroform phases give, after drying over anhydrous sodium sulphate, evaporation under reduced pressure and recrystallisation of the residue from ethanol, 1372 g. (4.34 mol) 7-(3-methanesulphonyloxypropyl)-theophylline of m.p. 112°–113°.

Elementary analysis: $C_{11}H_{16}N_4O_5S$ (316.34): calc.: C (41.77), H (5.10), N (17.71), S (10.13). found: C (41.98), H (5.15), N (17.72), S (10.1).

(b) 5-(3-Theophyllin-7-ylpropylamino)-5-desoxy-1.4;3.6-dianhydro-L-iditol

To a solution of 406 g. (2.8 mol) 5-amino-5-desoxy-1.4;3.6-dianhydro-L-iditol (prepared according to Example 1 b) in 1800 ml. ethanol, boiling under reflux, one adds within 6 hrs. 333 g. (1.05 mol) 7-(3-methanesulphonyloxypropyl)-theophylline, boils for a further 18 hrs. under reflux and then evaporates under reduced pressure. The residue is taken up in 1700 ml. water, adjusted to pH=9 by the addition of sodium hydroxide and the reaction product extracted by continuous extraction with chloroform in a rotary perforator. (Excess starting amine can be recovered from the aqueous phase). For further purification, one stirs the chloroform phase with 600 ml. 2 molar hydrochloric acid, discards the chloroform phase and removes from the hydrochloric acid solution unreacted 7-(3-methanesulphonyloxypropyl)-theophylline, as well as disubstitution product, by extraction with chloroform in a rotary perforator, whereby the pH value of the aqueous phase is gradually increased to pH=5 by the stepwise addition of sodium hydroxide. Subsequently, one adjusts the aqueous phase to pH=8, again perforates with chloroform, dries the chloroform extract over anhydrous sodium sulphate, filters and evaporates under reduced pressure. One obtains 316 g. (0.86 mol) of oily crude base. This is recrystallised, with the addition of 83 g. (0.86 mol) methanesulphonic acid, from ethanol/isopropanol and gives 346 g. (0.75 mol) crystalline 5-(3-theophyllin-7-ylpropylamino)-5-desoxy-1.4;3.6-dianhydro-L-iditol hydrogen methanesulphonate of m.p. 145°–147° and $[\alpha]_D^{25}$ 24.2 (c 0.5; water).

Elementary analysis: $C_{16}H_{23}N_5O_5 \times CH_3SO_3H$ (461.50): calc.: C (44.24), H (5.90), N (15.17), S (6.95). found: C (44.11), H (5.92), N (15.03), S (7.2).

(c) 5-(3-Theophyllin-7-ylpropylanino)-5-desoxy-1.4;3.6-dianhydro-L-iditol 2-nitrate With stirring and cooling to −15°, one slowly doses 40 g. (0.67 mol) urea to 600 ml. of 96% nitric acid (d=1.5; about 13.7 mol), subsequently adds thereto 254 g. (0.55 mol) 5-(3-theohyllin-7-ylpropylamino)-5-desoxy-1.4;3.6-dianhydro-L-iditol hydrogen mesylate in small portions and then stirs for 1 hr. at −15°.

The reaction solution is slowly stirred into about 1400 ml. water and brought to pH=8 by the dropwise addition of a solution of 550 g. (13.75 mol) sodium hydroxide in 2 liters of water, whereby, after the addition of about ¾ of the aqueous sodium hydroxide solution, 1 liter of chloroform is added thereto. One stirs up thoroughly, separates off the chloroform phase, extracts the aqueous phase again with 1 liter chloroform, washes the combined chloroform .ohases with 1 liter of water, dries over anhydrous sodium sulphate, filters and evaporates to dryness under reduced pressure at about 40° bath temperature. The so obtained 210 g. (0.51 mol) of crude base are dissolved in 700 ml. ethanol and mixed with a mixture of 45 ml. 37% hydrochloric acid (0.54 mol) and 200 ml. ethanol. Suction filtration and washing of the crystalline precipitate with 3×100 ml. ethanol and 1×100 ml. chloroform give, after drying in a vacuum cabinet at 50°, a total of 200 g. (0.448 mol) 5-(3-theophyllin-7-ylpropylamino)-5-desoxy-1.4;3.6-dianhydro-L-iditol 2-nitrate hydrochloride of m.p. 212°–214° (decomp.) and $[\alpha]_D^{25}$ 29.2 (c 0.5: water).

Elementary analysis: $C_{16}H_{22}N_6O_7 \times HCl$ (446.85): calc.: C (43.01), H (5.19), N (18.81), Cl (7.93). found: C (43.10), H (5.33), N (18.84), Cl (8.1).

As comparison compounds in the case of the investigation of the pharmacological properties of the compounds according to the invention, there was always used the commercially available compounds isosorbide dinitrate (ISDN) and isosorbide mononitrate (ISMN), whereby ISMN is 1.4;3.6-dianhydro-D-glucitol 2-nitrate.

The coronary flowthrough-increasing effectiveness of the compounds according to the invention was determined on isolated guinea pig hearts (isolated hearts according to Langendorff, method according to Bunger et al., Pflüger's Archiv. 353, 317–325 (1975)). After achieving the stationary state in the 30th minute, the hearts were each infused with 50 ml. tyrode solution with a content of test substance of, in each case, 25 μg./ml. Each test substance was tested on 3–6 hearts.

In each case, there was measured the inotropism, the flowthrough and the frequency, whereby the values given in Table I are average values of the percentage changes in comparison with the starting values. The comparison of the measured values shows that the coronary flowthrough-increasing effectiveness of the compounds according to the invention is greater than that of ISMN.

TABLE I

Experiments on Langendorff hearts
The values given in the Table show the percentage change in comparison with the initial value

| substance according to Example No. | inotropism | flowthrough | frequency |
|---|---|---|---|
| ISMN | −2.67 | +9.11 | −0.51 |
| 1d | −1.29 | +56.42 | −1.95 |
| 2 | −4.60 | +34.69 | +3.50 |
| 3 | −3.82 | +36.41 | −4.80 |
| 4 | −5.44 | +55.67 | −8.41 |
| 5 | −43.33 | +61.90 | −11.10 |
| 6 | +4.50 | +53.31 | +3.39 |
| 7c | +10.50 | +28.90 | ±0 |

TABLE I-continued

Experiments on Langendorff hearts
The values given in the Table show the percentage change
in comparison with the initial value

| substance according to Example No. | inotropism | flowthrough | frequency |
|---|---|---|---|
| 9c | −4.3 | +40.54 | ±0 |
| 10c | −6.4 | +13.00 | −5.6 |
| 13 | +2.3 | +12.20 | ±0 |
| 14 | +3.8 | +55.80 | ±0 |
| 15 | +3.85 | +47.10 | −3.45 |
| 16 | +6.50 | +22.50 | −6.80 |
| 17 | −11.50 | +60.60 | −3.60 |

The spasmolytic effectiveness of the compounds according to the invention was determined on isolated rat aorta preparations with noradrenalin-induced and+ contractions (method according to Wende and Peiper, Pflüger's Archiv 320, 133–141 (1970); and Towart and Stoepel, Naunyn Schmiedeberg's Archives of Pharmacology; suppl. Vol. 308, R 18 (1979)).
+ potassium chloride-induced In Table II there are given the concentrations of the test substances which are necessary for 50% inhibition of the spa $ED_{50}$ values). The spasmolytic effectivenesses of the compounds according to the invention are quite preponderantly better than those of ISMN and ISDN, especially when one takes into account the pharmacologically important relationship of the effective doses in the case of the noradrenalin and potassium chloride spasm.

The blood pressure-lowering effectiveness of the compounds according to the invention was measured in comparison with ISDN and ISMN on narcotised guinea pigs after i.v. administration. The values given in Table III show that the compound 1 d according to the invention is more effective than ISMN or ISDN.

TABLE II

| $ED^{50}$ values in mol/l. for spasmolytic actions | | |
|---|---|---|
| substance according to Example No. | Noradrenaline spasm | potassium chloride spasm |
| ISDN | $1.30 \times 10^{-6}$ | $3.10 \times 10^{-6}$ |
| ISMN | $1.60 \times 10^{-5}$ | $2.40 \times 10^{-6}$ |
| 1d | $5.60 \times 10^{-7}$ | $2.90 \times 10^{-6}$ |

TABLE II-continued

| $ED^{50}$ values in mol/l. for spasmolytic actions | | |
|---|---|---|
| substance according to Example No. | Noradrenaline spasm | potassium chloride spasm |
| 2 | $4.20 \times 10^{-6}$ | $3.05 \times 10^{-5}$ |
| 3 | $2.60 \times 10^{-6}$ | $3.60 \times 10^{-6}$ |
| 4 | $2.70 \times 10^{-6}$ | $3.80 \times 10^{-6}$ |
| 5 | $3.60 \times 10^{-7}$ | $2.40 \times 10^{-6}$ |
| 6 | $1.12 \times 10^{-6}$ | $1.80 \times 10^{-5}$ |
| 9c | $2.95 \times 10^{-6}$ | $4.59 \times 10^{-5}$ |
| 14 | $1.40 \times 10^{-6}$ | $4.39 \times 10^{-5}$ |

TABLE III

Blood pressure experiments on guinea pigs

| substance | dose mg/kg | blood pressure previously mm. Hg | blood pressure afterwards mm. Hg | Δ mm. Hg |
|---|---|---|---|---|
| ISDN | 0.25 | 68.70 ± 2.30 | 57.00 ± 2.10 | −11.70 |
|  | 1.00 | 66.00 ± 3.50 | 46.30 ± 0.90 | −19.70 |
|  | 2.50 | 66.70 ± 1.70 | 37.70 ± 0.90 | −29.00 |
| ISMN | 0.25 | 57.60 ± 3.10 | 53.90 ± 3.10 | −3.70 |
|  | 1.00 | 54.70 ± 3.80 | 48.40 ± 3.10 | −6.30 |
|  | 2.50 | 52.30 ± 4.80 | 41.40 ± 3.90 | −10.90 |
| 1d | 0.25 | 67.75 ± 3.27 | 49.75 ± 2.78 | −18.00 |
|  | 1.00 | 68.00 ± 3.85 | 40.00 ± 2.12 | −28.00 |
|  | 2.50 | 66.25 ± 2.66 | 37.50 ± 1.76 | −28.75 |

The inotropic and frequency-lowering heart circulation effectiveness of the compounds according to the invention was determined on mongrel cats of 2.5 to 3.5 kg. body weight with intravenous administration. The animals were narcotised with a mixture of chloralose-urethane (1.2 g./kg. urethane+40 mg./kg. chloralose administered i.p.). They breathed spontaneously through a tracheal canula. The A. carotis sinistra was used in order to place a catheter tip manometer into the left heart chamber. The V. jugularis served for injection purposes. Via the A. femoralis dextra, a catheter was pushed in up to the Aorta descendans and attached to a pressure recorder (Statham P 23 Db). The heart frequency was recorded with a pulse frequency measurer (Firm Hugo Sachs Elektronik) from the left ventricular pressure signal.

As follows from the values given in Table IV, the effectiveness of the tested compound according to the invention is better than that of the comparison compound ISDN.

TABLE IV

| substance | dose mg/kg | heart frequency previously | heart frequency afterwards | Δ | blood pressure previously | blood pressure afterwards | Δ | WD min | dp/dt previously | dp/dt afterwards | Δ | WD min |
|---|---|---|---|---|---|---|---|---|---|---|---|---|
| ISDN | 0.25 | 165.33 ± 7.96 | 171.67 ± 6.62 | +6.34 | 98.83 ± 6.07 | 81.17 ± 7.98 | −17.66 | 13.00 ± 4.52 | 7650 ± 585 | 8050 ± 1000 | +400 | — |
|  | 0.50 | 167.00 ± 8.18 | 173.33 ± 5.21 | +6.33 | 95.83 ± 4.56 | 73.67 ± 4.98 | −22.16 | 16.50 ± 6.91 | 7333 ± 344 | 7667 ± 1003 | +334 |  |
|  | 1.00 | 166.67 ± 9.53 | 174.33 ± 7.20 | +7.66 | 96.50 ± 3.88 | 69.17 ± 3.76 | −27.33 | 16.00 ± 3.41 | 6983 ± 367 | 7583 ± 1231 | +600 |  |
|  | 2.50 | 162.00 ± 8.18 | 170.67 ± 5.83 | +8.67 | 92.50 ± 4.37 | 60.67 ± 3.55 | −31.83 | >10 | 6450 ± 545 | 7567 ± 1540 | +1117 |  |
| 1d | 0.25 | 180.86 ± 7.06 | 184.57 ± 7.42 | +3.71 | 103.00 ± 5.01 | 64.86 ± 4.51 | −38.14 | 27.71 ± 5.38 | 7371 ± 997 | 6086 ± 967 | −1285 | 15.57 ± 5.68 |
|  | 0.50 | 178.29 ± 6.74 | 182.29 ± 7.92 | +4.00 | 101.86 ± 5.95 | 61.57 ± 4.92 | −40.29 | 20.21 ± 5.39 | 6614 ± 1006 | 5300 ± 988 | −1314 | 24.57 ± 7.02 |
|  | 1.00 | 174.00 ± 8.09 | 182.00 ± 9.49 | +8.00 | 103.43 ± 7.96 | 59.86 ± 5.67 | −43.57 | 24.29 ± 7.60 | 5957 ± 774 | 5186 ± 1005 | −771 | 19.58 ± 9.35 |
|  | 2.50 | 169.67 | 180.33 | +10.66 | 107.50 | 63.88 | −43.62 | >10 | 6383 | 6550 | +167 | 6.42 |

TABLE IV-continued

| sub-stance | dose mg/kg | heart frequency | | | blood pressure | | | WD min | dp/dt | | | WD min |
|---|---|---|---|---|---|---|---|---|---|---|---|---|
| | | previously | afterwards | Δ | previously | afterwards | Δ | | previously | afterwards | Δ | |
| | | ± 9.60 | ± 11.24 | | ± 8.80 | ± 7.09 | | | ± 556 | ± 1074 | | ± 1.62 |

Legend:
heart frequency, blood pressure and inotropism after intravenous administration of ISDN or substance 1d to cats
average values ± standard errors from groups of 6 animals Furthermore, the inotropic and frequency-lowering heart circulation effectiveness of the compounds according to the invention was determined on mongrel cats of 2.5 to 3.5 kg. body weight by intraduodenal administration. The animals were narcotised with a mixture of chloralose-urethane (1.2 g./kg. urethane+40 mg./kg. chloralose administered i.p.). They breathed spontaneously through a tracheal canula. The A. carotis sinistra was used in order to place a catheter tip manometer into the left heart chamber. The V. jugularis served for injection purposes. Via the A. femoralis, a catheter was pushed up into the Aorta descendans and attached to a pressure recorder (Statham P 23 Db). The heart frequency was recorded with a pulse frequency measurer (firm Hugo Sachs Elektronik) from the left ventricular pressure signal. A duodenal loop was exposed by a laparotomy. The substances to be tested were injected directly into the lumen.

As follows from the values given in Table V, the effectiveness of the tested compound according to the invention is better than that of the comparison compound ISDN.

For the continual measurement of the arterial blood pressure, the Arteria saphena dextra was exposed, the Arteria femoralis sinistra for the application of a Statham flow measurement head. A thermoprobe was pushed in from the Arteria brachialis sinistra into the aortal arc; it served for the measurement of the heart minute volume by means of the thermodilution method. With X-ray monitoring, a catheter tip manometer was introduced through the Arteria carotis dextra into the left ventricle and the left ventricular-end diastolic pressure determined therewith. Through the right Vena jugularis, a double-lumen catheter was introduced into the Arteria pulmonalis; via one lumen, ice-cooled isotonic NaCl solution was injected in for the determination of the heart minute volume, via the other the blood pressure in the Arteria pulmonalis was measured. Through a vein of the left front paw, a catheter was pushed into the right atrium for the measurement of pressure. With a differentiator, from! the pressure in the left ventricle, there was calculated the rate of pressure increase ("dp/dt") as a measure for contractability. After completion of the preparation, the animals were

TABLE V

| substance + dose | time (min) after admin. | frequency min$^{-1}$ | blood pressure | | dp/dt | |
|---|---|---|---|---|---|---|
| | | | mm. Hg | Δ | mm sec. | Δ |
| ISDN 5 mg/kg | 0 | 174.3 ± 9.3 | 104.3 ± 7.7 | | 8800 ± 831 | |
| | | | | −13.9 | | −800 |
| | 10 | 179.3 ± 7.7 | 90.4 ± 12.5 | | 8000 ± 1097 | |
| | | | | −13.1 | | −1133 |
| | 30 | 177.7 ± 7.7 | 91.2 ± 10.0 | | 766 ± 807 | |
| | | | | −10.1 | | −1167 |
| | 60 | 175.0 ± 8.6 | 94.2 ± 9.2 | | 7633 ± 743 | |
| | | | | −9.3 | | −1750 |
| | 120 | 166.7 ± 9.4 | 95.0 ± 9.6 | | 7050 ± 661 | |
| 1d 5 mg/kg | 0 | 173.2 ± 14.5 | 115.4 ± 14.4 | | 6000 ± 1367 | |
| | | | | −29.4 | | −1120 |
| | 10 | 173.6 ± 14.8 | 86.0 ± 13.8 | | 4880 ± 1371 | |
| | | | | −26.8 | | −1440 |
| | 30 | 166.0 ± 15.6 | 88.6 ± 14.8 | | 4500 ± 1312 | |
| | | | | −20.4 | | −980 |
| | 60 | 168.4 ± 14.0 | 95.0 ± 14.4 | | 5020 ± 1330 | |
| | | | | −16.0 | | −900 |
| | 120 | 164.8 ± 13.2 | 99.4 ± 13.2 | | 5100 ± 1341 | |

Legend:
heart frequency, blood pressure and inotropism at various times after intraduodenal administration of ISDN or substance 1d to cats.
average values ± standard errors on groups of 6 animals.

The circulatory pharmacological effectiveness of the compounds according to the invention was determined on narcotised dogs by intravenous administration. The investigations were carried out on mongrel dogs of both sexes, body weight 20.5 to 29 kg. After a twelve hour fasting period, the animals received on the morning of the experimental day 2 mg./kg. morphine s.c. About 30 minutes thereafter, narcosis was induced with 25 mg./kg. nembutal i.v. and maintained by continuous infusion with 5 mg./kg./h. The animals were constantly aerated through a tracheal tube with an $N_2O/O_2$ mixture (2:1). The $CO_2$ content of the expired air was measured continuously, the pH value of the blood about every 20 minutes.

anti-coagulated with 500 IU/kg. heparin. After a stabilising period of about 30 minutes, the heart minute volume was determined. Each of four animals then received 1 mg./kg. ISDN or 9c, 0.5 mg./kg. 1d administered i.v. The parameters of heart frequency, arterial blood pressure, pulmonalis pressure, pressure in the right atrium, left ventricular pressure, dp/dt and average femoralis flow were continuously recorded with a Beckmann 8-channel recorder. Furthermore, the heart minute volume was measured on the 2nd, 5th, 7th, 10th, 15th, 20th, 25th, 30th, 40th, 50th, 60th, 120th, 150th and 180th minute. All flow values and values derived therefrom were referred to a body weight of 20 kg. Heart capacities and resistances were calculated in the usual manner.

As follows from the values given in Tables VI, VII and VIII, the effectiveness of the compound according to the invention is better than that of the comparison compound ISDN. In particular, a long-lasting lowering of the arterial pressure and of the end diastolic pressure in the left ventricle was achieved.

Legend to Tables VI, VII and VIII

Circulatory pharmacological actions of ISDN (Tab. VI), 1d (Tab. VII) and 9c (Tab. VIII) on the dog after intravenous administration (1 mg./kg., ISDN and 9c; 0.5 mg./kg. 1d). Average values and standard errors from groups of 4 animals before the administration (v) or various times after the administration. HF: heart frequency (min$^{-1}$); AP$_{syst.}$, AP$_{diast.}$: systolic and diastolic aorta pressure (mm.Hg); PRV: pressure in the right atrium (mm.Hg); PAP: average pressure in the A. pulmonalis (mm.Hg); LVEDP: end diastolic pressure in the left ventricle (mm.Hg); dp/dt: rate of pressure increase in the left ventricle (mm.Hg/sec ); HL$_L$: heart capacity left, referred to 20 kg. body weight (W); HL$_R$: heart capacity right, referred to 20 kg. body weight (mW); SV: beat volume, referred to 20 kg. body weight (ml); BF$_{Fem}$: blood flow in the A. femoralis referred to 20 kg. body weight (ml./min.); W$_{Fem}$: moralis resistance, referred to 20 kg. body weight (KU); HZV: heart minute volume, referred to 20 kg. body weight (l/min); W$_{AP}$: pulmonalis resistance, referred to 20 kg. body weight (U); W$_{TP}$: total peripheral resistance, referred to 20 kg. body weight (U).

TABLE VI

| | ISDN (comparison) | | | | | | | |
|---|---|---|---|---|---|---|---|---|
| | v | 2 | 5 | 7 | 10 | 15 | 20 | 25 |
| HF | 109.5 ± 7.1 | 143.7 ± 5.1 | 133.5 ± 11.9 | 128.7 ± 11.1 | 121.7 ± 10.6 | 118.2 ± 9.8 | 112.5 ± 8.8 | 112.0 ± 8.5 |
| AP$_{syst}$ | 166.9 ± 4.9 | 145.7 ± 7.9 | 152.9 ± 6.4 | 152.9 ± 6.5 | 152.9 ± 5.6 | 154.8 ± 4.7 | 154.8 ± 5.6 | 156.6 ± 4.7 |
| AP$_{diast}$ | 95.6 ± 10.8 | 99.4 ± 9.7 | 102.2 ± 7.7 | 100.3 ± 8.0 | 98.4 ± 9.0 | 98.4 ± 9.0 | 96.6 ± 7.4 | 98.4 ± 7.2 |
| PRV | 2.06 ± 0.5 | 1.12 ± 0.6 | 1.72 ± 0.7 | 1.78 ± 0.7 | 1.87 ± 0.6 | 1.97 ± 0.7 | 2.15 ± 0.7 | 2.38 ± 0.8 |
| PAP | 14.3 ± 1.2 | 11.1 ± 0.7 | 11.5 ± 0.8 | 12.6 ± 1.4 | 12.6 ± 1.4 | 12.7 ± 1.6 | 12.6 ± 1.3 | 13.3 ± 1.5 |
| LVEDP | 7.69 ± 1.3 | 4.97 ± 1.1 | 5.81 ± 0.8 | 6.0 ± 0.9 | 6.28 ± 0.8 | 6.47 ± 0.7 | 6.75 ± 0.7 | 7.03 ± 0.7 |
| dp/dt | 2268.7 ± 271.1 | 2868.7 ± 370.4 | 2606.2 ± 30.1 | 2587.5 ± 291.0 | 2550.0 ± 302.2 | 2512.5 ± 288.0 | 2418.7 ± 281.2 | 2456.2 ± 295.9 |
| HL$_L$ | 0.76 ± 0.13 | 0.94 ± 0.15 | 0.95 ± 0.17 | 0.85 ± 0.14 | 0.84 ± 0.15 | 0.79 ± 0.14 | 0.78 ± 0.13 | 0.76 ± 0.13 |
| HL$_R$ | 85.1 ± 19.8 | 85.3 ± 11.3 | 81.4 ± 13.9 | 83.0 ± 18.3 | 82.4 ± 17.9 | 78.9 ± 21.3 | 75.3 ± 16.3 | 76.3 ± 18.2 |
| SV | 27.7 ± 2.8 | 26.3 ± 1.8 | 27.4 ± 2.1 | 25.9 ± 1.5 | 27.4 ± 1.9 | 26.8 ± 2.3 | 27.9 ± 2.3 | 26.8 ± 2.1 |
| BF$_{Fem}$ | 44.9 ± 11.7 | 31.2 ± 6.5 | 35.4 ± 7.7 | 37.3 ± 7.1 | 38.4 ± 6.6 | 40.9 ± 8.6 | 40.9 ± 7.2 | 41.9 ± 8.5 |
| W$_{Fem}$ | 0.39 ± 0.1 | 0.55 ± 0.1 | 0.49 ± 0.1 | 0.45 ± 0.1 | 0.42 ± 0.05 | 0.41 ± 0.1 | 0.40 ± 0.05 | 0.40 ± 0.1 |
| HZV | 3.03 ± 0.4 | 3.8 ± 0.4 | 3.7 ± 0.5 | 3.3 ± 0.4 | 3.4 ± 0.4 | 3.2 ± 0.4 | 3.1 ± 0.4 | 3.0 ± 0.4 |
| W$_{AP}$ | 0.31 ± 0.05 | 0.23 ± 0.05 | 0.22 ± 0.04 | 0.27 ± 0.03 | 0.26 ± 0.03 | 0.26 ± 0.03 | 0.25 ± 0.02 | 0.27 ± 0.02 |
| W$_{TP}$ | 5.27 ± 0.4 | 4.02 ± 0.1 | 4.39 ± 0.4 | 4.72 ± 0.3 | 4.66 ± 0.3 | 4.96 ± 0.3 | 4.92 ± 0.3 | 5.22 ± 0.4 |
| | 30 | 40 | 50 | 60 | 90 | 120 | 150 | 180 |
| HF | 110.0 ± 17.5 | 108.0 ± 9.8 | 109.2 ± 21.2 | 107.5 ± 10.1 | 109.5 ± 9.9 | 104.2 ± 7.7 | 103.7 ± 6.9 | 103.7 ± 5.9 |
| AP$_{syst}$ | 155.6 ± 3.2 | 158.4 ± 4.9 | 157.5 ± 5.1 | 159.4 ± 5.8 | 163.2 ± 5.8 | 161.2 ± 6.6 | 161.2 ± 4.7 | 161.2 ± 4.8 |
| AP$_{diast}$ | 98.1 ± 5.9 | 101.2 ± 6.5 | 101.2 ± 6.5 | 101.2 ± 6.5 | 99.4 ± 5.6 | 97.5 ± 5.5 | 95.6 ± 4.5 | 95.6 ± 5.6 |
| PRV | 2.34 ± 0.7 | 2.34 ± 0.7 | 2.29 ± 0.6 | 2.53 ± 0.7 | 2.53 ± 0.7 | 2.81 ± 0.8 | 3.0 ± 0.9 | 2.81 ± 0.8 |
| PAP | 13.5 ± 1.5 | 14.0 ± 1.5 | 14.0 ± 1.6 | 14.1 ± 1.6 | 14.6 ± 1.8 | 15.0 ± 2.0 | 14.6 ± 1.5 | 15.5 ± 1.6 |
| LVEDP | 7.22 ± 0.6 | 7.60 ± 0.7 | 7.60 ± 0.7 | 7.77 ± 0.7 | 7.98 ± 0.9 | 8.34 ± 1.0 | 7.78 ± 1.0 | 7.60 ± 1.2 |
| dp/dt | 2390.6 ± 284.9 | 2343.7 ± 281.2 | 2306.2 ± 269.2 | 2250.0 ± 250.6 | 2231.2 ± 251.2 | 2118.7 ± 221.5 | 2025.0 ± 181.1 | 2043.7 ± 206.2 |
| HL$_L$ | 0.76 ± 0.10 | 0.76 ± 0.13 | 0.77 ± 0.13 | 0.78 ± 0.14 | 0.77 ± 0.12 | 0.72 ± 0.10 | 0.74 ± 0.10 | 0.79 ± 0.12 |
| HL$_R$ | 78.6 ± 16.5 | 80.5 ± 17.2 | 81.1 ± 18.6 | 81.9 ± 20.1 | 85.4 ± 20.5 | 81.5 ± 18.9 | 79.7 ± 17.2 | 92.4 ± 18.7 |
| SV | 27.8 ± 2.1 | 27.7 ± 1.9 | 27.4 ± 1.6 | 28.2 ± 1.6 | 27.7 ± 1.9 | 28.1 ± 1.8 | 28.6 ± 1.6 | 30.6 ± 1.9 |
| BF$_{Fem}$ | 41.5 ± 8.1 | 42.9 ± 8.2 | 43.9 ± 9.2 | 42.3 ± 8.9 | 44.4 ± 8.2 | 49.3 ± 7.7 | 51.3 ± 9.8 | 53.7 ± 10.8 |
| W$_{Fem}$ | 0.40 ± 0.1 | 0.40 ± 0.05 | 0.39 ± 0.1 | 0.41 ± 0.1 | 0.38 ± 0.04 | 0.33 ± 0.03 | 0.32 ± 0.05 | 0.32 ± 0.06 |
| HZV | 3.0 ± 0.3 | 3.0 ± 0.3 | 3.0 ± 0.4 | 3.0 ± 0.4 | 3.0 ± 0.4 | 2.9 ± 0.2 | 3.0 ± 0.3 | 3.2 ± 0.3 |

TABLE VI-continued

ISDN (comparison)

| | | | | | | | | |
|---|---|---|---|---|---|---|---|---|
| $W_{AP}$ | 0.27 ± 0.03 | 0.28 ± 0.04 | 0.27 ± 0.04 | 0.26 ± 0.03 | 0.27 ± 0.06 | 0.28 ± 0.08 | 0.29 ± 0.05 | 0.31 ± 0.05 |
| $W_{TP}$ | 5.13 ± 0.4 | 5.41 ± 0.5 | 5.38 ± 0.5 | 5.32 ± 0.5 | 5.35 ± 0.6 | 5.36 ± 0.3 | 5.22 ± 0.3 | 4.89 ± 0.3 |

TABLE VII

Compound according to Example 1d

| | v | 2 | 5 | 7 | 10 | 15 | 20 | 25 |
|---|---|---|---|---|---|---|---|---|
| HF | 101.2 ± 9.6 | 145.7 ± 24.1 | 131.2 ± 20.3 | 119.5 ± 16.5 | 110.2 ± 14.5 | 107.7 ± 13.1 | 104.0 ± 10.1 | 103.7 ± 8.9 |
| $AP_{syst}$ | 152.8 ± 12.0 | 107.8 ± 8.0 | 119.4 ± 5.2 | 122.8 ± 6.4 | 124.7 ± 8.3 | 126.0 ± 6.3 | 127.9 ± 6.6 | 127.5 ± 5.5 |
| $AP_{diast}$ | 76.9 ± 4.5 | 67.5 ± 3.4 | 77.8 ± 5.2 | 75.9 ± 5.2 | 74.6 ± 5.5 | 75.9 ± 3.2 | 78.7 ± 2.6 | 79.7 ± 1.8 |
| PRV | 3.09 ± 0.56 | 0.37 ± 0.15 | 0.60 ± 0.20 | 1.12 ± 0.37 | 1.22 ± 0.41 | 1.59 ± 0.41 | 1.78 ± 0.46 | 2.25 ± 0.63 |
| $\overline{PAP}$ | 15.59 ± 1.19 | 11.25 ± 1.03 | 11.44 ± 1.22 | 11.75 ± 1.40 | 11.90 ± 1.43 | 12.19 ± 1.38 | 12.37 ± 1.08 | 12.53 ± 0.85 |
| LVEDP | 7.50 ± 0.61 | 3.85 ± 0.23 | 4.78 ± 0.32 | 5.16 ± 0.46 | 4.69 ± 0.24 | 4.97 ± 0.28 | 5.62 ± 0.34 | 5.44 ± 0.32 |
| dp/dt | 1903.1 ± 188.3 | 2915.6 ± 247.0 | 2671.9 ± 185.8 | 2662.5 ± 206.5 | 2465.6 ± 396.9 | 2465.6 ± 389.8 | 2428.1 ± 385.1 | 2353.1 ± 371.0 |
| $HL_L$ | 0.50 ± 0.09 | 0.51 ± 0.09 | 0.47 ± 0.07 | 0.47 ± 0.06 | 0.47 ± 0.07 | 0.44 ± 0.06 | 0.45 ± 0.06 | 0.45 ± 0.06 |
| $HL_R$ | 67.1 ± 12.7 | 70.9 ± 10.6 | 58.2 ± 9.5 | 56.8 ± 9.2 | 57.1 ± 10.3 | 53.8 ± 10.1 | 52.8 ± 8.1 | 50.9 ± 7.1 |
| SV | 23.4 ± 2.5 | 21.9 ± 4.3 | 19.6 ± 3.5 | 21.3 ± 3.5 | 22.9 ± 3.6 | 22.0 ± 3.6 | 22.3 ± 3.4 | 22.3 ± 3.6 |
| $BF_{Fem}$ | 51.5 ± 10.8 | 42.6 ± 10.0 | 40.8 ± 8.2 | 42.7 ± 7.7 | 46.2 ± 8.6 | 48.3 ± 9.7 | 51.5 ± 10.5 | 52.9 ± 9.0 |
| $W_{Fem}$ | 0.29 ± 0.05 | 0.28 ± 0.05 | 0.32 ± 0.05 | 0.30 ± 0.04 | 0.28 ± 0.05 | 0.28 ± 0.06 | 0.27 ± 0.05 | 0.27 ± 0.05 |
| HZV | 2.35 ± 0.29 | 2.94 ± 0.34 | 2.40 ± 0.24 | 2.40 ± 0.22 | 2.38 ± 0.23 | 2.26 ± 0.25 | 2.24 ± 0.25 | 2.24 ± 0.29 |
| $W_{AP}$ | 0.46 ± 0.04 | 0.35 ± 0.06 | 0.38 ± 0.07 | 0.37 ± 0.08 | 0.41 ± 0.07 | 0.43 ± 0.07 | 0.41 ± 0.06 | 0.44 ± 0.07 |
| $W_{TP}$ | 5.78 ± 0.53 | 3.73 ± 0.23 | 5.16 ± 0.40 | 5.10 ± 0.38 | 5.10 ± 0.35 | 5.51 ± 0.47 | 5.71 ± 0.47 | 5.78 ± 0.64 |

| | 30 | 40 | 50 | 60 | 90 | 120 | 150 | 180 |
|---|---|---|---|---|---|---|---|---|
| HF | 101.2 ± 8.3 | 97.5 ± 7.2 | 96.2 ± 6.9 | 95.5 ± 5.3 | 92.5 ± 7.6 | 96.5 ± 10.5 | 104.5 ± 7.3 | 114.0 ± 6.0 |
| $AP_{syst}$ | 130.9 ± 5.8 | 133.1 ± 6.9 | 135.9 ± 8.1 | 136.8 ± 7.6 | 137.8 ± 9.8 | 139.7 ± 9.4 | 139.7 ± 10.0 | 137.8 ± 12.9 |
| $AP_{diast}$ | 81.6 ± 2.8 | 83.4 ± 3.2 | 85.9 ± 3.3 | 88.5 ± 3.7 | 92.8 ± 5.6 | 95.2 ± 4.7 | 92.8 ± 5.6 | 90.9 ± 6.4 |
| PRV | 2.34 ± 0.66 | 2.15 ± 0.60 | 2.25 ± 0.65 | 2.40 ± 0.65 | 3.19 ± 0.83 | 3.47 ± 0.85 | 3.97 ± 0.79 | 4.22 ± 0.80 |
| $\overline{PAP}$ | 12.81 ± 0.78 | 13.34 ± 0.71 | 13.37 ± 0.58 | 13.87 ± 0.52 | 13.81 ± 0.28 | 13.5 ± 0.46 | 14.41 ± 0.39 | 14.41 ± 0.62 |
| LVEDP | 5.72 ± 0.28 | 6.0 ± 0.34 | 6.47 ± 0.54 | 8.06 ± 0.77 | 9.47 ± 0.60 | 9.47 ± 0.65 | 10.12 ± 0.66 | 10.5 ± 0.81 |
| dp/dt | 2306.2 ± 346.6 | 2193.7 ± 322.0 | 2006.2 ± 244.2 | 1968.7 ± 297.4 | 1743.7 ± 277.9 | 1659.4 ± 303.2 | 1640.6 ± 264.4 | 1621.9 ± 228.8 |
| $HL_L$ | 0.45 ± 0.06 | 0.43 ± 0.05 | 0.41 ± 0.05 | 0.39 ± 0.05 | 0.34 ± 0.04 | 0.35 ± 0.04 | 0.35 ± 0.04 | 0.37 ± 0.05 |
| $HL_R$ | 50.5 ± 7.3 | 50.8 ± 7.5 | 47.3 ± 6.4 | 46.0 ± 6.6 | 36.7 ± 4.9 | 34.9 ± 4.8 | 36.9 ± 4.1 | 38.3 ± 2.7 |
| SV | 22.1 ± 3.8 | 21.5 ± 3.2 | 20.5 ± 3.2 | 19.4 ± 3.0 | 17.4 ± 2.8 | 17.0 ± 3.1 | 15.9 ± 2.8 | 15.5 ± 2.1 |
| $BF_{Fem}$ | 54.1 ± 8.8 | 58.5 ± 10.7 | 62.2 ± 11.9 | 62.6 ± 13.2 | 57.4 ± 12.4 | 49.9 ± 11.2 | 49.5 ± 11.2 | 50.9 ± 10.3 |
| $W_{Fem}$ | 0.26 ± 0.05 | 0.25 ± 0.05 | 0.25 ± 0.06 | 0.26 ± 0.06 | 0.29 ± 0.07 | 0.36 ± 0.12 | 0.37 ± 0.13 | 0.32 ± 0.08 |
| HZV | 2.18 ± 0.29 | 2.05 ± 0.25 | 1.93 ± 0.25 | 1.82 ± 0.25 | 1.57 ± 0.20 | 1.57 ± 0.19 | 1.61 ± 0.20 | 1.73 ± 0.17 |
| $W_{AP}$ | 0.45 ± 0.07 | 0.50 ± 0.06 | 0.50 ± 0.08 | 0.46 ± 0.09 | 0.39 ± 0.08 | 0.35 ± 0.04 | 0.37 ± 0.05 | 0.32 ± 0.06 |
| $W_{TP}$ | 6.10 ± 0.68 | 6.62 ± 0.75 | 7.24 ± 0.87 | 7.90 ± 1.09 | 9.39 ± 1.45 | 9.56 ± 1.45 | 8.10 ± 1.37 | 8.13 ± 0.95 |

TABLE VIII

| Compound according to Example 9c | | | | | | | |
|---|---|---|---|---|---|---|---|
| v | 2 | 5 | 7 | 10 | 15 | 20 | 25 |

| | v | 2 | 5 | 7 | 10 | 15 | 20 | 25 |
|---|---|---|---|---|---|---|---|---|
| HF | 102.5 ± 5.9 | 163.2 ± 14.9 | 129.7 ± 2.3 | 123.2 ± 3.3 | 120.5 ± 3.7 | 115.2 ± 3.9 | 114.5 ± 3.1 | 112.5 ± 3.2 |
| $AP_{syst}$ | 147.2 ± 9.8 | 105.0 ± 13.3 | 126.6 ± 5.7 | 129.4 ± 5.6 | 127.5 ± 6.8 | 128.4 ± 6.2 | 128.4 ± 7.5 | 131.2 ± 7.9 |
| $AP_{diast}$ | 78.7 ± 6.5 | 58.1 ± 6.9 | 79.7 ± 3.2 | 82.5 ± 4.3 | 81.6 ± 4.9 | 81.6 ± 3.9 | 82.5 ± 5.5 | 83.4 ± 4.9 |
| PRV | 3.0 ± 0.53 | 0.90 ± 1.01 | 0.88 ± 0.69 | 1.16 ± 0.55 | 1.12 ± 0.55 | 1.63 ± 0.53 | 1.41 ± 0.47 | 1.46 ± 0.46 |
| $\overline{PAP}$ | 13.6 ± 0.8 | 10.6 ± 0.4 | 11.6 ± 0.7 | 11.5 ± 0.4 | 12.0 ± 0.9 | 11.8 ± 0.8 | 11.8 ± 0.9 | 11.4 ± 1.0 |
| LVEDP | 7.60 ± 1.0 | 3.60 ± 0.87 | 4.64 ± 1.35 | 4.92 ± 1.15 | 4.92 ± 1.20 | 5.20 ± 1.10 | 5.48 ± 1.18 | 5.62 ± 1.12 |
| dp/dt | 1837.5 ± 195.4 | 3045.0 ± 412.3 | 2287.5 ± 191.8 | 2325.0 ± 214.9 | 2306.2 ± 197.5 | 2250.0 ± 188.1 | 2221.9 ± 223.5 | 2221.9 ± 252.7 |
| $HL_L$ | 0.56 ± 0.09 | 0.51 ± 0.12 | 0.56 ± 0.10 | 0.58 ± 0.09 | 0.57 ± 0.10 | 0.57 ± 0.08 | 0.55 ± 0.09 | 0.56 ± 0.10 |
| $HL_R$ | 63.08 ± 11.5 | 67.6 ± 8.2 | 66.9 ± 13.8 | 64.2 ± 10.2 | 68.8 ± 14.8 | 63.6 ± 9.8 | 63.1 ± 12.1 | 60.5 ± 12.8 |
| SV | 25.9 ± 3.2 | 20.0 ± 3.2 | 21.1 ± 2.7 | 22.4 ± 2.5 | 23.0 ± 2.3 | 24.2 ± 2.5 | 23.3 ± 2.4 | 23.7 ± 3.0 |
| $BF_{Fem}$ | 48.0 ± 6.9 | 34.6 ± 10.1 | 39.1 ± 9.1 | 42.5 ± 10.4 | 41.9 ± 6.1 | 43.4 ± 6.4 | 44.2 ± 6.2 | 41.3 ± 6.3 |
| $W_{Fem}$ | 0.29 ± 0.04 | 0.33 ± 0.08 | 0.37 ± 0.08 | 0.34 ± 0.06 | 0.32 ± 0.04 | 0.31 ± 0.04 | 0.31 ± 0.04 | 0.33 ± 0.03 |
| HZV | 2.62 ± 0.28 | 3.15 ± 0.32 | 2.73 ± 0.32 | 2.75 ± 0.27 | 2.76 ± 0.27 | 2.77 ± 0.24 | 2.65 ± 0.25 | 2.65 ± 0.28 |
| $W_{AP}$ | 0.29 ± 0.06 | 0.30 ± 0.04 | 0.33 ± 0.06 | 0.31 ± 0.04 | 0.32 ± 0.06 | 0.30 ± 0.05 | 0.30 ± 0.06 | 0.27 ± 0.07 |
| $W_{TP}$ | 5.15 ± 0.65 | 3.07 ± 0.18 | 4.72 ± 0.35 | 4.77 ± 0.25 | 4.68 ± 0.23 | 4.65 ± 0.23 | 4.90 ± 0.26 | 5.00 ± 0.29 |

| | 30 | 40 | 50 | 60 | 90 | 120 | 150 | 180 |
|---|---|---|---|---|---|---|---|---|
| HF | 111.5 ± 3.0 | 109.2 ± 2.5 | 105.5 ± 3.2 | 103.2 ± 3.5 | 98.0 ± 3.4 | 96.7 ± 2.0 | 98.2 ± 1.2 | 100.0 ± 1.8 |
| $AP_{syst}$ | 134.1 ± 7.2 | 136.9 ± 8.3 | 142.5 ± 8.5 | 144.7 ± 8.2 | 148.1 ± 7.6 | 150.0 ± 7.6 | 148.7 ± 6.9 | 148.1 ± 5.8 |
| $AP_{diast}$ | 81.6 ± 4.9 | 86.2 ± 5.5 | 88.2 ± 5.6 | 88.2 ± 4.9 | 90.9 ± 3.9 | 90.9 ± 3.5 | 88.7 ± 3.2 | 87.2 ± 3.5 |
| PRV | 1.65 ± 0.63 | 1.63 ± 0.38 | 1.78 ± 0.62 | 1.97 ± 0.64 | 2.53 ± 0.73 | 3.0 ± 0.85 | 3.10 ± 0.67 | 3.28 ± 0.77 |
| $\overline{PAP}$ | 11.5 ± 0.8 | 11.8 ± 1.0 | 11.8 ± 1.0 | 12.0 ± 0.9 | 13.3 ± 1.2 | 14.2 ± 1.6 | 15.0 ± 1.7 | 15.5 ± 2.0 |
| LVEDP | 5.62 ± 1.0 | 5.62 ± 0.89 | 6.19 ± 0.98 | 6.47 ± 1.04 | 7.03 ± 1.05 | 7.73 ± 1.15 | 7.87 ± 1.07 | 7.87 ± 1.0 |
| dp/dt | 2221.9 ± 243.7 | 2203.1 ± 255.0 | 2165.6 ± 262.7 | 2109.4 ± 229.3 | 1987.5 ± 264.3 | 1837.5 ± 213.2 | 1809.4 ± 236.4 | 1743.7 ± 176.9 |
| $HL_L$ | 0.57 ± 0.09 | 0.60 ± 0.10 | 0.61 ± 0.10 | 0.59 ± 0.09 | 0.56 ± 0.08 | 0.55 ± 0.08 | 0.54 ± 0.06 | 0.55 ± 0.05 |
| $HL_R$ | 60.5 ± 11.7 | 63.2 ± 12.7 | 61.7 ± 12.2 | 59.1 ± 11.0 | 59.2 ± 10.8 | 60.8 ± 10.8 | 64.4 ± 10.3 | 67.5 ± 8.6 |
| SV | 24.2 ± 2.5 | 24.9 ± 1.5 | 25.5 ± 2.7 | 25.1 ± 2.5 | 24.8 ± 2.5 | 24.7 ± 2.1 | 24.3 ± 1.8 | 24.8 ± 1.3 |
| $BF_{Fem}$ | 44.2 ± 6.6 | 44.2 ± 5.8 | 26.6 ± 6.2 | 45.8 ± 6.8 | 41.7 ± 6.7 | 39.9 ± 5.6 | 39.0 ± 9.5 | 42.8 ± 4.8 |
| $W_{Fem}$ | 0.31 ± 0.03 | 0.32 ± 0.03 | 0.31 ± 0.03 | 0.32 ± 0.03 | 0.36 ± 0.04 | 0.38 ± 0.04 | 0.37 ± 0.03 | 0.33 ± 0.03 |
| HZV | 2.68 ± 0.23 | 2.71 ± 0.26 | 2.68 ± 0.25 | 2.59 ± 0.24 | 2.42 ± 0.24 | 2.39 ± 0.20 | 2.38 ± 0.15 | 2.47 ± 0.09 |
| $W_{AP}$ | 0.28 ± 0.06 | 0.30 ± 0.06 | 0.26 ± 0.07 | 0.27 ± 0.07 | 0.33 ± 0.08 | 0.35 ± 0.10 | 0.40 ± 0.11 | 0.41 ± 0.13 |
| $W_{TP}$ | 4.87 ± 0.17 | 5.05 ± 0.21 | 5.24 ± 0.18 | 5.48 ± 0.29 | 6.00 ± 0.31 | 6.07 ± 0.26 | 5.92 ± 0.15 | 5.61 ± 0.04 |

For informing examination of acute toxicity of some of the compounds according to the invention, said compounds were intravenously administered in physiological saline solution to female NMRI-albino mice in doses of 50, 100 and 200 mg/kg, respectively. The compounds were injected to at least 3 animals per dose. If no animal had yet been died following to the highest dose which was administered, no more doses of substances were tested. In case of doubt, the examination was repeated with at least 3 more animals applying the same dose.

The rate of death within 24 hours after administration was observed.

In table IX, the determined rates of death as well as the $LD_{50}$-ranges evaluated therefrom are shown.

TABLE IX

| Compound according to example | Frequency of death with an intravenous dose of | | | Evaluated $LD_{50}$-range (mg/kg) |
|---|---|---|---|---|
| | 200 mg/kg | 100 mg/kg | 50 mg/kg | |
| 2 | 1/3 | 0/3 | — | ≧200 |
| 3 | 0/6 | — | — | >200 |
| 4 | 10/10 | 0/10 | — | 100–200 |

TABLE IX-continued

| Compound according to example | Frequency of death with an intravenous dose of | | | Evaluated LD$_{50}$-range (mg/kg) |
|---|---|---|---|---|
| | 200 mg/kg | 100 mg/kg | 50 mg/kg | |
| 5 | 10/10 | 4/10 | 0/10 | ≧100 |
| 7c | 0/6 | — | — | >200 |
| 8c | 11/13 | 0/3 | — | 100–200 |
| 10c | 0/6 | — | — | >200 |
| 11d | 0/6 | — | — | >200 |
| 12d | 0/6 | — | — | >200 |
| 13 | 0/6 | — | — | >200 |
| 15 | 3/3 | 3/3 | 3/3 | <50 |
| 16 | 10/10 | 0/10 | — | 100–200 |
| 17 | 3/3 | 2/3 | 0/10 | 50–100 |

As to example 1d, the following values for acute toxicity were determined with a greater number of mice, according to the method of Lichtfield and Wilcoxon:

LD$_{50}$ i.v. = 219 mg/kg (190.4–251.9)
LD$_{50}$ i.p. = 760 mg/kg (678.6–851.2)
LD$_{50}$ p.o. = 1600 mg/kg

We claim:

1. Alkylaminodesoxy-1.4;3.6-dianhydrohexitol nitrates substituted by purine bases having the formula

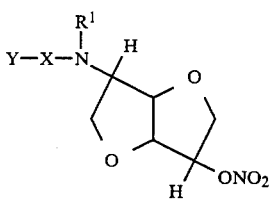

wherein $R^1$ signifies a hydrogen atom or lower alkyl with 1 to 4 C-atoms, X is a straight-chained, branched alkyl, or hydroxyalkyl, with 1 to 7 C-atoms, Y is 1,3-dialkylxanthin-7-yl, a 3,7-dialkylxanthin-1-yl group, each with straight or branched-chained alkyl groups having 1 to 5 C-atoms, and their physiologically acceptable acid-addition salts.

2. 5-Alkylamino-5-desoxy-1.4;3.6-dianhydro-L-iditol 2-nitrates substituted by purine bases having the formula

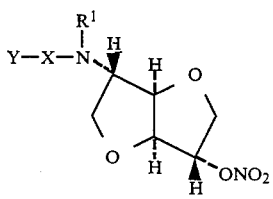

wherein $R^1$, X and Y possesses the meanings given in claim 1, and their physiologically acceptable acid-addition salts.

3. 5-Alkylamino-5-desoxy-1.4;3.6-dianhydro-D-glucitol 2-nitrates/substituted by purine bases having the formula VI

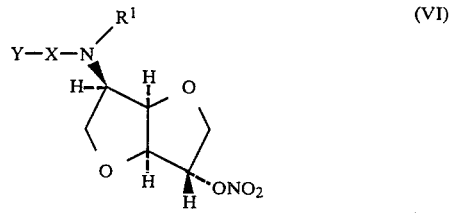

wherein $R^1$, X and Y possess the meanings given in claim 1, and their physiologically acceptable acid-addition salts.

4. 2-Alkylamino-2-desoxy-1.4;3.6-dianhydro-D-glucitol 5 nitrates substituted by purine bases having the formula

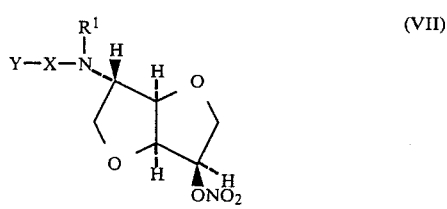

wherein $R^1$, X and Y possess the meanings given in claim 1, and their physiologically acceptable acid-addition salts.

5. 5-Alkylamino-5-desoxy-1.4;3.6-dianhydro-D-mannitol 2-nitrates substituted by purine bases having the formula

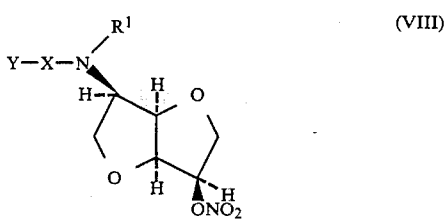

wherein $R^1$, X and Y possess the meanings given in claim 1, and their physiologically acceptable acid-addition salts.

6. 5-(3-Theophyllin-7-ylpropyl)-amino-5-desoxy-1.4;3.6-dianhydro-L-iditol 2-nitrate.
7. 5-(2-Theophyllin-7-ylethyl)-amino-5-desoxy-1.4;3.6-dianhydro-L-iditol 2-nitrate.
8. 5-(4-Theophyllin-7-ylbutyl)-amino-5-desoxy-1.4;3.6-dianhydro-L-iditol 2-nitrate.
9. 5-(5-Theophyllin-7-ylpentyl)-amino-5-desoxy-1.4;3.6-dianhydro-L-iditol 2-nitrate.
10. 5-(6-Theophyllin-7-ylhexyl)-amino-5-desoxy-1.4;3.6-dianhydro-L-iditol 2-nitrate.
11. 5-(2-Hydroxy-3-theophyllin-7-ylpropyl)-amino-5-desoxy-1.4;3.6-dianhydro-L-iditol 2-nitrate.
12. 5-[3 (3,7-Dimethylxanthin-1-yl)-propylamino]-5-desoxy-1.4;3.6-dianhydro-L-iditol 2-nitrate.
13. 5-[3-(3-Isobutyl-1-methylxanthin-7-yl)-propylamino]-desoxy-1.4;3.6-dianhydro-L-iditol 2-nitrate.
14. 5-[N-Methyl-N-(3-theophyllin-7-ylpropyl)-amino]-5-desoxy-1.4;3.6-dianhydro-L-iditol 2-nitrate.
15. 5-[1-Methyl-3-(theophyllin-7-yl)-propylamino]-5-desoxy-1.4;3.6-dianhydro-L-iditol 2-nitrate.

16. (+)-5-[1-Methyl-3-(theophyllin-7-yl)-propylamino]-5-desoxy-1.4:3.6-dianhydro-L-iditol 2-nitrate.

17. (−)-5-[1-Methyl-3-(theophyllin-7-yl)-propylamino]-5-desoxy-1.4;3.6-dianhydro-L-iditol 2-nitrate.

18. 5-[1-Methyl-5-(theophyllin-7-yl)-pentylamino]-desoxy-1.4;3.6-dianhydro-L-iditol 2-nitrate.

19. 5-(3-Theophyllin-7-ylpropyl)-amino-5-desoxy-1.4;3.6-dianhydro-D-glucitol 2-nitrate.

20. 2-(3-Theophyllin-7-ylpropyl)-amino-2-desoxy-1.4;3.6-dianhydro-D-glucitol 5-nitrate.

21. 5-(3-Theophyllin-7-ylpropyl)-amino-5-desoxy-1.4;3.6-dianhydro-D-mannitol 2-nitrate.

22. A composition comprising a pharmaceutically effective amount of the nitrate of claim 1 and pharmaceutically acceptable carriers therefor.

* * * * *

UNITED STATES PATENT AND TRADEMARK OFFICE
CERTIFICATE OF CORRECTION

PATENT NO. : 4,542,137
DATED : September 17, 1985
INVENTOR(S) : Klaus Klessing and Shyam S. Chatterjee It is certified that error appears in the above-identified patent and that said Letters Patent is hereby corrected as shown below:

Column 1, change structural formula (II) to read as follows:

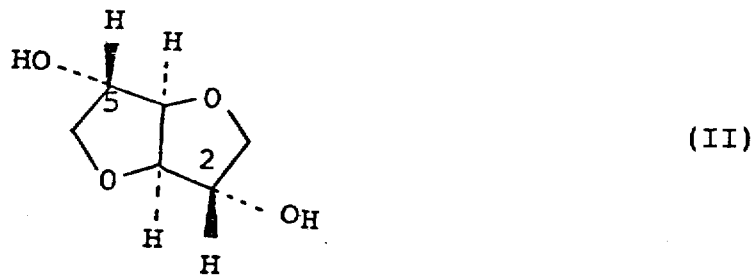
(II)

Signed and Sealed this

Twenty-sixth Day of August 1986

[SEAL]

Attest:

DONALD J. QUIGG

Attesting Officer

Commissioner of Patents and Trademarks